US011817095B2

(12) United States Patent
Vozila et al.

(10) Patent No.: US 11,817,095 B2
(45) Date of Patent: *Nov. 14, 2023

(54) AMBIENT COOPERATIVE INTELLIGENCE SYSTEM AND METHOD

(71) Applicant: Nuance Communications, Inc., Burlington, MA (US)

(72) Inventors: Paul Joseph Vozila, Arlington, MA (US); Neal Snider, Belmont, MA (US)

(73) Assignee: Nuance Communications, Inc., Burlington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/592,353

(22) Filed: Feb. 3, 2022

(65) Prior Publication Data

US 2022/0199082 A1 Jun. 23, 2022

Related U.S. Application Data

(63) Continuation of application No. 17/133,199, filed on Dec. 23, 2020, now Pat. No. 11,250,855.

(51) Int. Cl.
*G10L 15/22* (2006.01)
*G06N 20/00* (2019.01)
(Continued)

(52) U.S. Cl.
CPC .............. *G10L 15/22* (2013.01); *G06N 20/00* (2019.01); *G10L 15/1815* (2013.01); *G10L 2015/088* (2013.01); *G10L 2015/223* (2013.01)

(58) Field of Classification Search
CPC ................. G10L 15/22; G10L 15/1815; G10L 2015/088; G10L 2015/223; G06N 20/00;
(Continued)

(56) References Cited

U.S. PATENT DOCUMENTS 6,651,043 B2  11/2003  Ammicht
8,185,400 B1   5/2012  Goffin
(Continued)

OTHER PUBLICATIONS

"International Search Report and Written Opinion issued in PCT Application No. PCT/US21/064701", dated Jan. 21, 2022, 8 Pages.
(Continued)

*Primary Examiner* — Abul K Azad
(74) *Attorney, Agent, or Firm* — Brian J. Colandreo; Heath M. Sargeant; Holland & Knight LLP

(57) ABSTRACT

A method, computer program product, and computing system for monitoring a plurality of conversations within a monitored space to generate a conversation data set; processing the conversation data set using machine learning to: define a system-directed command for an ACI system, and associate one or more conversational contexts with the system-directed command; detecting the occurrence of a specific conversational context within the monitored space, wherein the specific conversational context is included in the one or more conversational contexts associated with the system-directed command; and executing, in whole or in part, functionality associated with the system-directed command in response to detecting the occurrence of the specific conversational context without requiring the utterance of the system-directed command and/or a wake-up word/phrase.

18 Claims, 8 Drawing Sheets

(51) Int. Cl.
*G10L 15/18* (2013.01)
*G10L 15/08* (2006.01)

(58) Field of Classification Search
CPC ....... G06F 40/284; G06F 40/30; G16H 10/60; G16H 50/70; G16H 80/00
See application file for complete search history.

(56) References Cited

U.S. PATENT DOCUMENTS

| | | | |
|---|---|---|---|
| 10,529,321 | B2 | 1/2020 | Shriberg |
| 10,747,894 | B1 | 8/2020 | Cine |
| 10,847,149 | B1 | 11/2020 | Mok |
| 11,250,855 | B1 * | 2/2022 | Vozila ................... G06N 20/00 |
| 2012/0035931 | A1 * | 2/2012 | LeBeau ............. H04M 1/72403 |
| | | | 704/E15.005 |
| 2012/0245944 | A1 | 9/2012 | Gruber |
| 2013/0144616 | A1 * | 6/2013 | Bangalore ............... G10L 15/20 |
| | | | 704/226 |
| 2018/0233139 | A1 | 8/2018 | Finkelstein |

OTHER PUBLICATIONS

Elkan, et al., "Learning Classifiers from Only Positive and Unlabeled Data", (pp. 213-220, KDD'08, Aug. 24-27, 2008, Las Vegas, Nevada.).

Norouzian, et al., "Exploring Attention Mechanism for Acoustic-Based Classification of Speech Utterances Into System-Directed and Non-System-Directed", (pp. 1-5, Feb. 1, 2019.).

* cited by examiner

AMBIENT COOPERATIVE INTELLIGENCE SYSTEM AND METHOD

RELATED APPLICATION

This application is a continuation of U.S. patent application Ser. No. 17/133,199 filed Dec. 23, 2020, the contents of which is incorporated herein by reference.

TECHNICAL FIELD

This disclosure relates to intelligence systems and methods and, more particularly, to ambient cooperative intelligence systems and methods.

BACKGROUND

As is known in the art, cooperative intelligence is the creation of reports and documentation that details the history of an event/individual. As would be expected, traditional documentation includes various types of data, examples of which may include but are not limited to paper-based documents and transcripts, as well as various images and diagrams.

As the world moved from paper-based content to digital content, traditional documentation also moved in that direction, where reports and documentation were gradually transitioned from stacks of paper geographically-dispersed across multiple locations/institutions to consolidated and readily accessible digital content.

SUMMARY OF DISCLOSURE

In one implementation, a computer-implemented method is executed on a computing device and includes: monitoring a plurality of conversations within a monitored space to generate a conversation data set; processing the conversation data set using machine learning to: define a system-directed command for an ACI system, and associate one or more conversational contexts with the system-directed command; detecting the occurrence of a specific conversational context within the monitored space, wherein the specific conversational context is included in the one or more conversational contexts associated with the system-directed command; and executing, in whole or in part, functionality associated with the system-directed command in response to detecting the occurrence of the specific conversational context without requiring the utterance of the system-directed command and/or a wake-up word/phrase.

One or more of the following features may be included. Defining a system-directed command for an ACI system may include: monitoring for the occurrence of the wake-up word/phrase; identifying a command that follows the wake-up word/phrase; and defining the system-directed command as the command that follows the wake-up word/phrase. Associating one or more conversational contexts with the system-directed command may include: identifying the subject matter of a conversation preceding the occurrence of the wake-up word/phrase; and defining at least one of the conversational contexts based, at least in part, upon the subject matter of the conversation preceding the occurrence of the wake-up word/phrase. Executing, in whole or in part, functionality associated with the system-directed command in response to detecting the occurrence of the specific conversational context may include: automatically executing functionality associated with the system-directed command in response to detecting the occurrence of the specific conversational context. Executing, in whole or in part, functionality associated with the system-directed command in response to detecting the occurrence of the specific conversational context may include: inquiring about execution of the functionality associated with system-directed command in response to detecting the occurrence of the specific conversational context. Executing, in whole or in part, functionality associated with the system-directed command in response to detecting the occurrence of the specific conversational context may include: recommending the execution of one or more supplemental operations in response to detecting the occurrence of the specific conversational context.

In another implementation, a computer program product resides on a computer readable medium and has a plurality of instructions stored on it. When executed by a processor, the instructions cause the processor to perform operations including: monitoring a plurality of conversations within a monitored space to generate a conversation data set; processing the conversation data set using machine learning to: define a system-directed command for an ACI system, and associate one or more conversational contexts with the system-directed command; detecting the occurrence of a specific conversational context within the monitored space, wherein the specific conversational context is included in the one or more conversational contexts associated with the system-directed command; and executing, in whole or in part, functionality associated with the system-directed command in response to detecting the occurrence of the specific conversational context without requiring the utterance of the system-directed command and/or a wake-up word/phrase.

One or more of the following features may be included. Defining a system-directed command for an ACI system may include: monitoring for the occurrence of the wake-up word/phrase; identifying a command that follows the wake-up word/phrase; and defining the system-directed command as the command that follows the wake-up word/phrase. Associating one or more conversational contexts with the system-directed command may include: identifying the subject matter of a conversation preceding the occurrence of the wake-up word/phrase; and defining at least one of the conversational contexts based, at least in part, upon the subject matter of the conversation preceding the occurrence of the wake-up word/phrase. Executing, in whole or in part, functionality associated with the system-directed command in response to detecting the occurrence of the specific conversational context may include: automatically executing functionality associated with the system-directed command in response to detecting the occurrence of the specific conversational context. Executing, in whole or in part, functionality associated with the system-directed command in response to detecting the occurrence of the specific conversational context may include: inquiring about execution of the functionality associated with system-directed command in response to detecting the occurrence of the specific conversational context. Executing, in whole or in part, functionality associated with the system-directed command in response to detecting the occurrence of the specific conversational context may include: recommending the execution of one or more supplemental operations in response to detecting the occurrence of the specific conversational context.

In another implementation, a computing system includes a processor and memory is configured to perform operations including: monitoring a plurality of conversations within a monitored space to generate a conversation data set; processing the conversation data set using machine learning to:

define a system-directed command for an ACI system, and associate one or more conversational contexts with the system-directed command; detecting the occurrence of a specific conversational context within the monitored space, wherein the specific conversational context is included in the one or more conversational contexts associated with the system-directed command; and executing, in whole or in part, functionality associated with the system-directed command in response to detecting the occurrence of the specific conversational context without requiring the utterance of the system-directed command and/or a wake-up word/phrase.

One or more of the following features may be included. Defining a system-directed command for an ACI system may include: monitoring for the occurrence of the wake-up word/phrase; identifying a command that follows the wake-up word/phrase; and defining the system-directed command as the command that follows the wake-up word/phrase. Associating one or more conversational contexts with the system-directed command may include: identifying the subject matter of a conversation preceding the occurrence of the wake-up word/phrase; and defining at least one of the conversational contexts based, at least in part, upon the subject matter of the conversation preceding the occurrence of the wake-up word/phrase. Executing, in whole or in part, functionality associated with the system-directed command in response to detecting the occurrence of the specific conversational context may include: automatically executing functionality associated with the system-directed command in response to detecting the occurrence of the specific conversational context. Executing, in whole or in part, functionality associated with the system-directed command in response to detecting the occurrence of the specific conversational context may include: inquiring about execution of the functionality associated with system-directed command in response to detecting the occurrence of the specific conversational context. Executing, in whole or in part, functionality associated with the system-directed command in response to detecting the occurrence of the specific conversational context may include: recommending the execution of one or more supplemental operations in response to detecting the occurrence of the specific conversational context.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

System Overview

Figure 1:
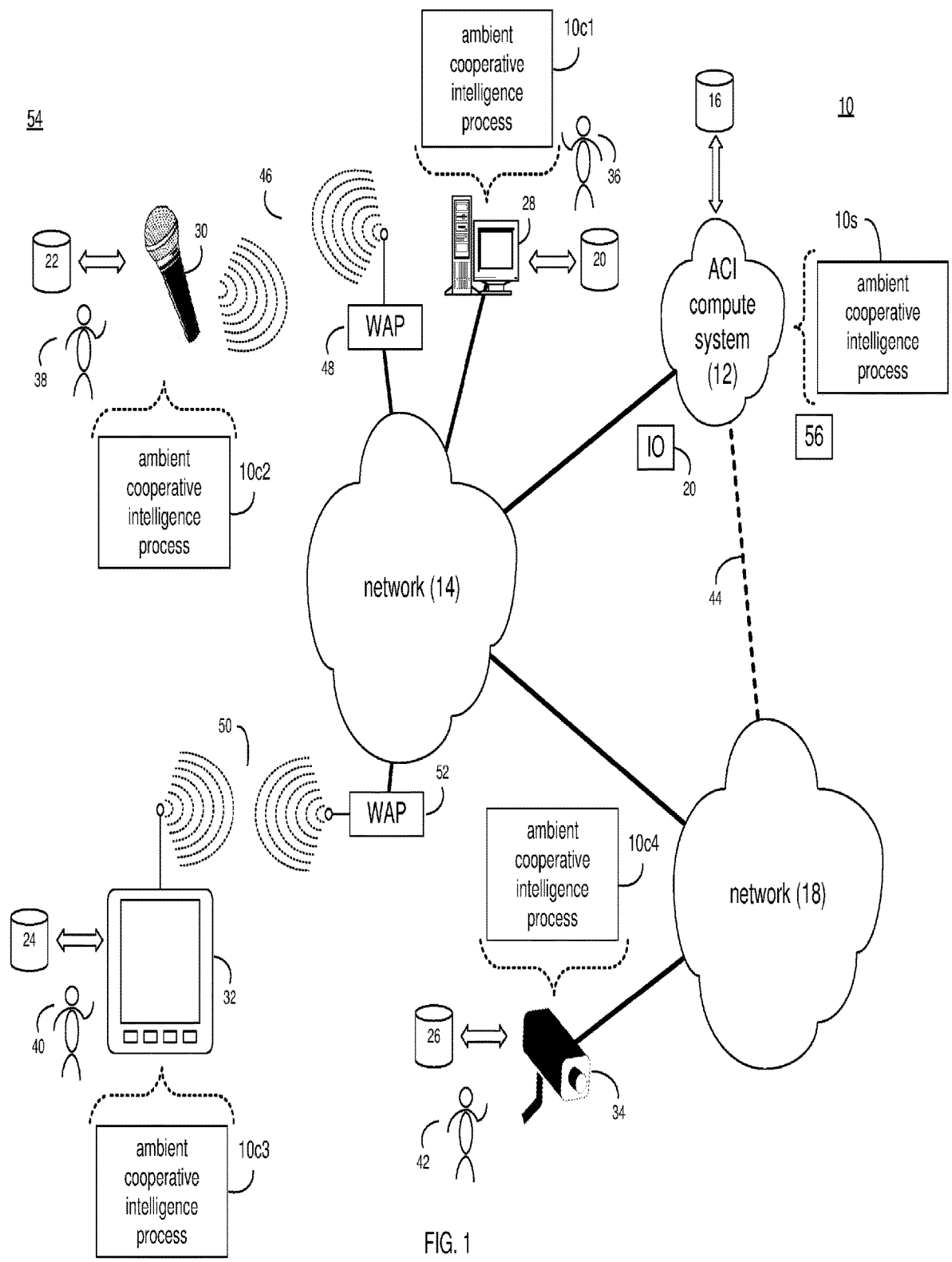
FIG. 1 is a diagrammatic view of an ambient cooperative intelligence compute system and an ambient cooperative intelligence process coupled to a distributed computing network.

Referring to FIG. 1, there is shown ambient cooperative intelligence process 10. As will be discussed below in greater detail, ambient cooperative intelligence process 10 may be configured to automate the collection and processing of encounter information to generate/store/distribute reports.

Ambient cooperative intelligence process 10 may be implemented as a server-side process, a client-side process, or a hybrid server-side/client-side process. For example, ambient cooperative intelligence process 10 may be implemented as a purely server-side process via ambient cooperative intelligence process 10s. Alternatively, ambient cooperative intelligence process 10 may be implemented as a purely client-side process via one or more of ambient cooperative intelligence process 10c1, ambient cooperative intelligence process 10c2, ambient cooperative intelligence process 10c3, and ambient cooperative intelligence process 10c4. Alternatively still, ambient cooperative intelligence process 10 may be implemented as a hybrid server-side/client-side process via ambient cooperative intelligence process 10s in combination with one or more of ambient cooperative intelligence process 10c1, ambient cooperative intelligence process 10c2, ambient cooperative intelligence process 10c3, and ambient cooperative intelligence process 10c4.

Accordingly, ambient cooperative intelligence process 10 as used in this disclosure may include any combination of ambient cooperative intelligence process 10s, ambient cooperative intelligence process 10c1, ambient cooperative intelligence process 10c2, ambient cooperative intelligence process 10c3, and ambient cooperative intelligence process 10c4.

Ambient cooperative intelligence process 10s may be a server application and may reside on and may be executed by ambient cooperative intelligence (ACI) compute system 12, which may be connected to network 14 (e.g., the Internet or a local area network). ACI compute system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

As is known in the art, a SAN may include one or more of a personal computer, a server computer, a series of server computers, a mini computer, a mainframe computer, a RAID device and a NAS system. The various components of ACI compute system 12 may execute one or more operating systems, examples of which may include but are not limited to: Microsoft Windows Server™; Redhat Linux™, Unix, or a custom operating system, for example.

The instruction sets and subroutines of ambient cooperative intelligence process 10s, which may be stored on storage device 16 coupled to ACI compute system 12, may be executed by one or more processors (not shown) and one or more memory architectures (not shown) included within ACI compute system 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Various IO requests (e.g. IO request 20) may be sent from ambient cooperative intelligence process 10s, ambient cooperative intelligence process 10c1, ambient cooperative intelligence process 10c2, ambient cooperative intelligence process 10c3 and/or ambient cooperative intelligence process 10c4 to ACI compute system 12. Examples of IO request 20 may include but are not limited to data write requests (i.e. a request that content be written to ACI compute system 12) and data read requests (i.e. a request that content be read from ACI compute system 12).

The instruction sets and subroutines of ambient cooperative intelligence process 10c1, ambient cooperative intelligence process 10c2, ambient cooperative intelligence process 10c3 and/or ambient cooperative intelligence process 10c4, which may be stored on storage devices 20, 22, 24, 26 (respectively) coupled to ACI client electronic devices 28, 30, 32, 34 (respectively), may be executed by one or more processors (not shown) and one or more memory architectures (not shown) incorporated into ACI client electronic devices 28, 30, 32, 34 (respectively). Storage devices 20, 22, 24, 26 may include but are not limited to: hard disk drives; optical drives; RAID devices; random access memories (RAM); read-only memories (ROM), and all forms of flash memory storage devices. Examples of ACI client electronic devices 28, 30, 32, 34 may include, but are not limited to, personal computing device 28 (e.g., a smart phone, a personal digital assistant, a laptop computer, a notebook computer, and a desktop computer), audio input device 30 (e.g., a handheld microphone, a lapel microphone, an embedded microphone (such as those embedded within eyeglasses, smart phones, tablet computers and/or watches) and an audio recording device), display device 32 (e.g., a tablet computer, a computer monitor, and a smart television), machine vision input device 34 (e.g., an RGB imaging system, an infrared imaging system, an ultraviolet imaging system, a laser imaging system, a SONAR imaging system, a RADAR imaging system, and a thermal imaging system), a hybrid device (e.g., a single device that includes the functionality of one or more of the above-references devices; not shown), an audio rendering device (e.g., a speaker system, a headphone system, or an earbud system; not shown), various medical devices (e.g., medical imaging equipment, heart monitoring machines, body weight scales, body temperature thermometers, and blood pressure machines; not shown), and a dedicated network device (not shown).

Users 36, 38, 40, 42 may access ACI compute system 12 directly through network 14 or through secondary network 18. Further, ACI compute system 12 may be connected to network 14 through secondary network 18, as illustrated with link line 44.

The various ACI client electronic devices (e.g., ACI client electronic devices 28, 30, 32, 34) may be directly or indirectly coupled to network 14 (or network 18). For example, personal computing device 28 is shown directly coupled to network 14 via a hardwired network connection. Further, machine vision input device 34 is shown directly coupled to network 18 via a hardwired network connection. Audio input device 30 is shown wirelessly coupled to network 14 via wireless communication channel 46 established between audio input device 30 and wireless access point (i.e., WAP) 48, which is shown directly coupled to network 14. WAP 48 may be, for example, an IEEE 802.11a, 802.11b, 802.11g, 802.11n, Wi-Fi, and/or Bluetooth device that is capable of establishing wireless communication channel 46 between audio input device 30 and WAP 48. Display device 32 is shown wirelessly coupled to network 14 via wireless communication channel 50 established between display device 32 and WAP 52, which is shown directly coupled to network 14.

The various ACI client electronic devices (e.g., ACI client electronic devices 28, 30, 32, 34) may each execute an operating system, examples of which may include but are not limited to Microsoft Windows™, Apple Macintosh™, Redhat Linux™, or a custom operating system, wherein the combination of the various ACI client electronic devices (e.g., ACI client electronic devices 28, 30, 32, 34) and ACI compute system 12 may form modular ACI system 54.

The Ambient Cooperative Intelligence System

While ambient cooperative intelligence process 10 will be described below as being utilized to automate the collection and processing of clinical encounter information to generate/store/distribute medical records, this is for illustrative purposes only and is not intended to be a limitation of this disclosure, as other configurations are possible and are considered to be within the scope of this disclosure.

Figure 2:
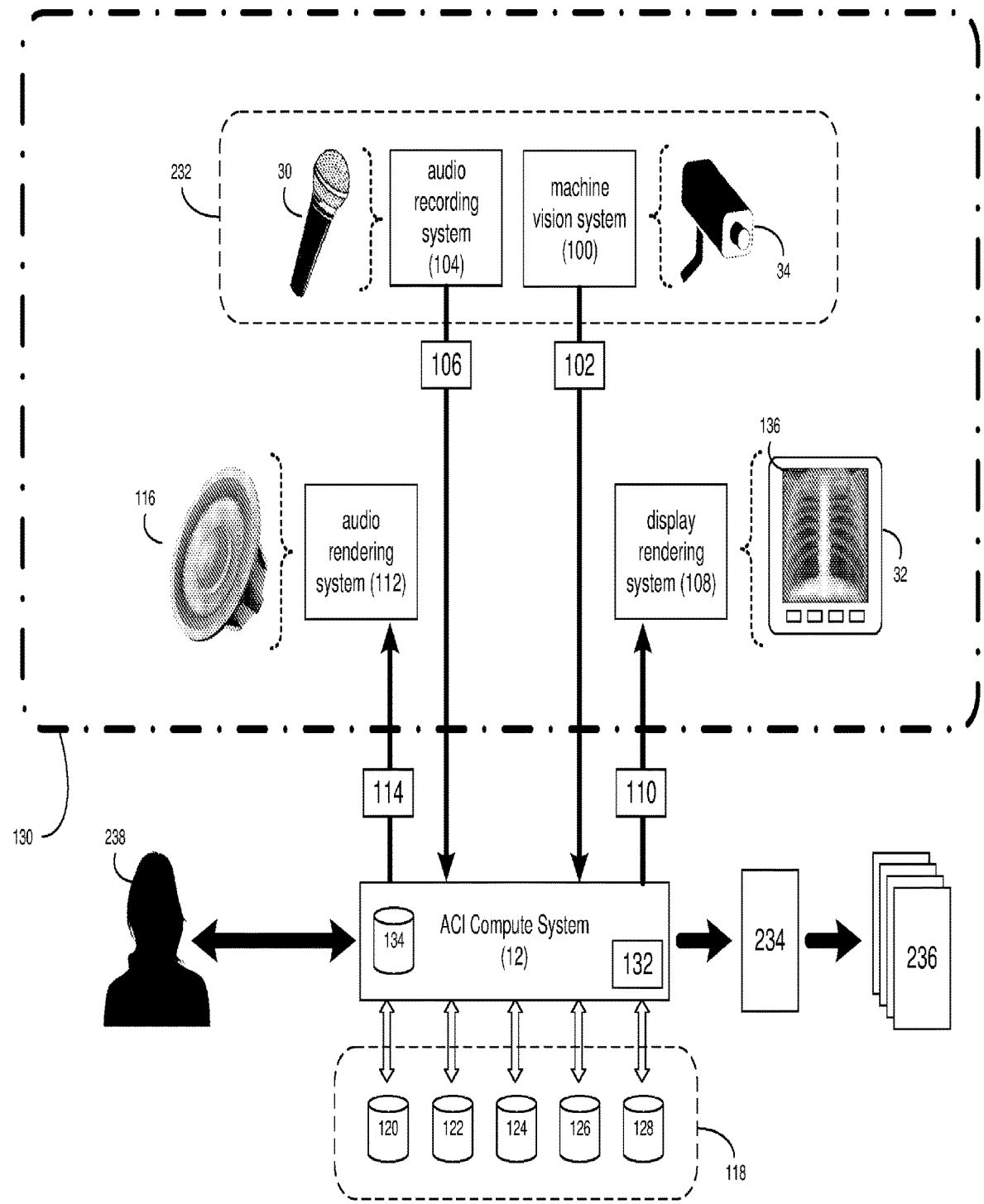
FIG. 2 is a diagrammatic view of a modular ACI system incorporating the ambient cooperative intelligence compute system of FIG. 1.

Referring also to FIG. 2, there is shown a simplified exemplary embodiment of modular ACI system 54 that is configured to automate cooperative intelligence. Modular ACI system 54 may include: machine vision system 100 configured to obtain machine vision encounter information 102 concerning a patient encounter; audio recording system 104 configured to obtain audio encounter information 106 concerning the patient encounter; and a compute system (e.g., ACI compute system 12) configured to receive machine vision encounter information 102 and audio encounter information 106 from machine vision system 100 and audio recording system 104 (respectively). Modular ACI system 54 may also include: display rendering system 108 configured to render visual information 110; and audio rendering system 112 configured to render audio information 114, wherein ACI compute system 12 may be configured to provide visual information 110 and audio information 114 to display rendering system 108 and audio rendering system 112 (respectively).

Example of machine vision system 100 may include but are not limited to: one or more ACI client electronic devices (e.g., ACI client electronic device 34, examples of which may include but are not limited to an RGB imaging system, an infrared imaging system, a ultraviolet imaging system, a laser imaging system, a SONAR imaging system, a RADAR imaging system, and a thermal imaging system). Examples of audio recording system 104 may include but are not limited to: one or more ACI client electronic devices (e.g., ACI client electronic device 30, examples of which may include but are not limited to a handheld microphone (e.g., one example of a body worn microphone), a lapel microphone (e.g., another example of a body worn microphone), an embedded microphone, such as those embedded within eyeglasses, smart phones, tablet computers and/or watches (e.g., another example of a body worn microphone), and an audio recording device). Examples of display rendering system 108 may include but are not limited to: one or more ACI client electronic devices (e.g., ACI client electronic device 32, examples of which may include but are not limited to a tablet computer, a computer monitor, and a smart television). Examples of audio rendering system 112 may include but are not limited to: one or more ACI client electronic devices (e.g., audio rendering device 116, examples of which may include but are not limited to a speaker system, a headphone system, and an earbud system).

ACI compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the ambient speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, a physical events datasource, and a home healthcare datasource. While in this particular example, five different examples of datasources 118 are shown, this is for illustrative purposes only and is not intended to be a limitation of this disclosure, as other configurations are possible and are considered to be within the scope of this disclosure.

As will be discussed below in greater detail, modular ACI system 54 may be configured to monitor a monitored space (e.g., monitored space 130) in a clinical environment, wherein examples of this clinical environment may include but are not limited to: a doctor's office, a medical facility, a medical practice, a medical lab, an urgent care facility, a medical clinic, an emergency room, an operating room, a hospital, a long term care facility, a rehabilitation facility, a nursing home, and a hospice facility. Accordingly, an example of the above-referenced patient encounter may include but is not limited to a patient visiting one or more of the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility).

Machine vision system 100 may include a plurality of discrete machine vision systems when the above-described clinical environment is larger or a higher level of resolution is desired. As discussed above, examples of machine vision system 100 may include but are not limited to: one or more ACI client electronic devices (e.g., ACI client electronic device 34, examples of which may include but are not limited to an RGB imaging system, an infrared imaging system, an ultraviolet imaging system, a laser imaging system, a SONAR imaging system, a RADAR imaging system, and a thermal imaging system). Accordingly, machine vision system 100 may include one or more of each of an RGB imaging system, an infrared imaging systems, an ultraviolet imaging systems, a laser imaging system, a SONAR imaging system, a RADAR imaging system, and a thermal imaging system.

Audio recording system 104 may include a plurality of discrete audio recording systems when the above-described clinical environment is larger or a higher level of resolution is desired. As discussed above, examples of audio recording system 104 may include but are not limited to: one or more ACI client electronic devices (e.g., ACI client electronic device 30, examples of which may include but are not limited to a handheld microphone, a lapel microphone, an embedded microphone (such as those embedded within eyeglasses, smart phones, tablet computers and/or watches) and an audio recording device). Accordingly, audio recording system 104 may include one or more of each of a handheld microphone, a lapel microphone, an embedded microphone (such as those embedded within eyeglasses, smart phones, tablet computers and/or watches) and an audio recording device.

Display rendering system 108 may include a plurality of discrete display rendering systems when the above-described clinical environment is larger or a higher level of resolution is desired. As discussed above, examples of display rendering system 108 may include but are not limited to: one or more ACI client electronic devices (e.g., ACI client electronic device 32, examples of which may include but are not limited to a tablet computer, a computer monitor, and a smart television). Accordingly, display rendering system 108 may include one or more of each of a tablet computer, a computer monitor, and a smart television.

Audio rendering system 112 may include a plurality of discrete audio rendering systems when the above-described clinical environment is larger or a higher level of resolution is desired. As discussed above, examples of audio rendering system 112 may include but are not limited to: one or more ACI client electronic devices (e.g., audio rendering device 116, examples of which may include but are not limited to a speaker system, a headphone system, or an earbud system). Accordingly, audio rendering system 112 may include one or more of each of a speaker system, a headphone system, or an earbud system.

ACI compute system 12 may include a plurality of discrete compute systems. As discussed above, ACI compute system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform. Accordingly, ACI compute system 12 may include one or more of each of a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

Microphone Array

Figure 3:
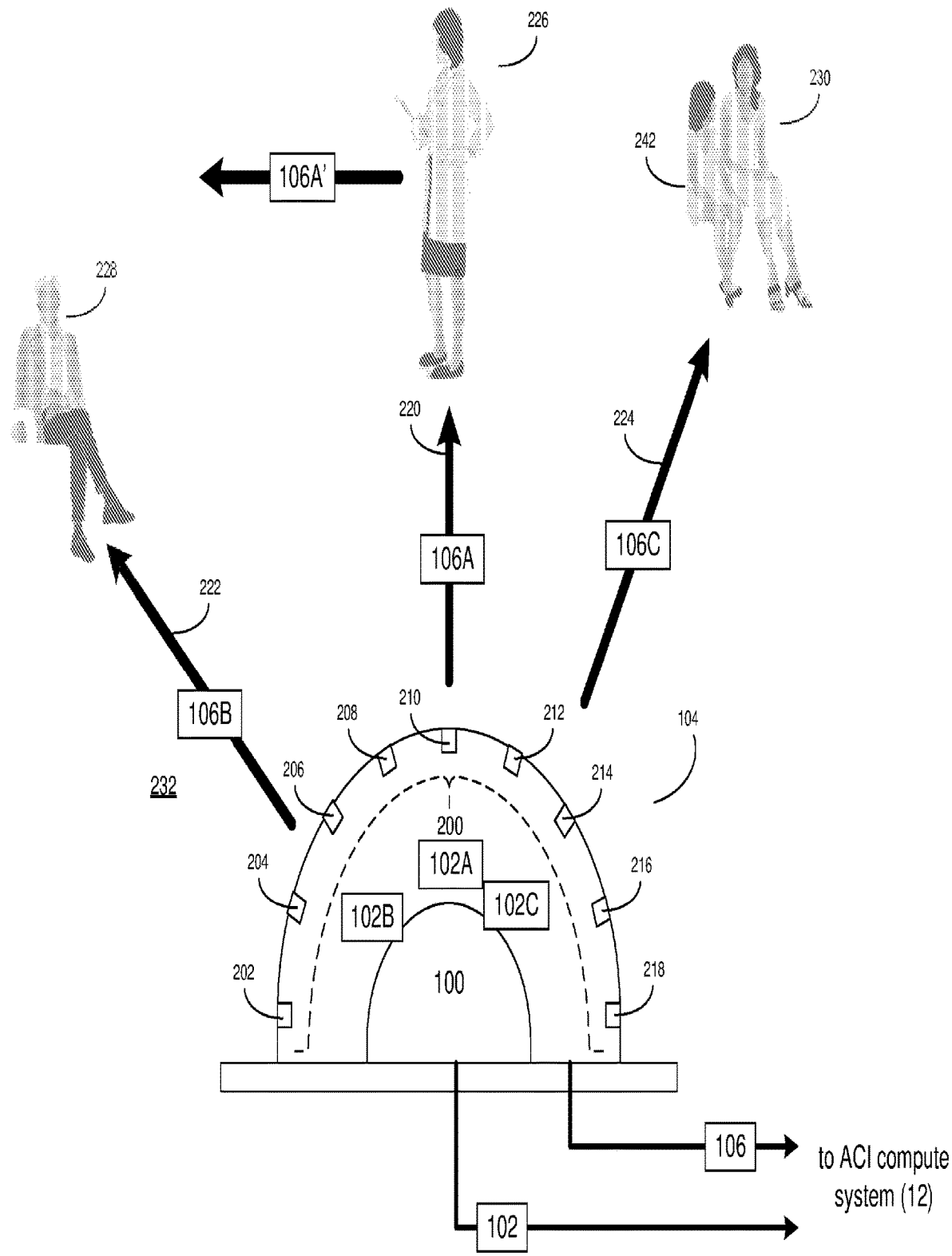
FIG. 3 is a diagrammatic view of a mixed-media ACI device included within the modular ACI system of FIG. 2.

Referring also to FIG. 3, audio recording system 104 may include microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. As will be discussed below in greater detail, modular ACI system 54 may be configured to form one or more audio recording beams (e.g., audio recording beams 220, 222, 224) via the discrete audio acquisition devices (e.g., audio acquisition devices 202, 204, 206, 208, 210, 212, 214, 216, 218) included within audio recording system 104.

For example, modular ACI system 54 may be further configured to steer the one or more audio recording beams (e.g., audio recording beams 220, 222, 224) toward one or more encounter participants (e.g., encounter participants 226, 228, 230) of the above-described patient encounter. Examples of the encounter participants (e.g., encounter participants 226, 228, 230) may include but are not limited to: medical professionals (e.g., doctors, nurses, physician's assistants, lab technicians, physical therapists, scribes (e.g., a transcriptionist) and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

Accordingly, modular ACI system 54 and/or audio recording system 104 may be configured to utilize one or more of the discrete audio acquisition devices (e.g., audio acquisition devices 202, 204, 206, 208, 210, 212, 214, 216, 218) to form an audio recording beam. For example, modular ACI system 54 and/or audio recording system 104 may be configured to utilize various audio acquisition devices to form audio recording beam 220, thus enabling the capturing of audio (e.g., speech) produced by encounter participant 226 (as audio recording beam 220 is pointed to (i.e., directed toward) encounter participant 226). Additionally, modular ACI system 54 and/or audio recording system 104 may be configured to utilize various audio acquisition devices to form audio recording beam 222, thus enabling the capturing of audio (e.g., speech) produced by encounter participant 228 (as audio recording beam 222 is pointed to (i.e., directed toward) encounter participant 228). Additionally, modular ACI system 54 and/or audio recording system 104 may be configured to utilize various audio acquisition devices to form audio recording beam 224, thus enabling the capturing of audio (e.g., speech) produced by encounter participant 230 (as audio recording beam 224 is pointed to (i.e., directed toward) encounter participant 230).

Further, modular ACI system 54 and/or audio recording system 104 may be configured to utilize null-steering precoding to cancel interference between speakers and/or noise. As is known in the art, null-steering precoding is a method of spatial signal processing by which a multiple antenna transmitter may null multiuser interference signals in wireless communications, wherein null-steering precoding may mitigate the impact off background noise and unknown user interference. In particular, null-steering precoding may be a method of beamforming for narrowband signals that may compensate for delays of receiving signals from a specific source at different elements of an antenna array. In general and to improve performance of the antenna array, incoming signals may be summed and averaged, wherein certain signals may be weighted and compensation may be made for signal delays.

Machine vision system 100 and audio recording system 104 may be stand-alone devices (as shown in FIG. 2). Additionally/alternatively, machine vision system 100 and audio recording system 104 may be combined into one package to form mixed-media ACI device 232. For example, mixed-media ACI device 232 may be configured to be mounted to a structure (e.g., a wall, a ceiling, a beam, a column) within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility), thus allowing for easy installation of the same. Further, modular ACI system 54 may be configured to include a plurality of mixed-media ACI devices (e.g., mixed-media ACI device 232) when the above-described clinical environment is larger or a higher level of resolution is desired.

Modular ACI system 54 may be further configured to steer the one or more audio recording beams (e.g., audio recording beams 220, 222, 224) toward one or more encounter participants (e.g., encounter participants 226, 228, 230) of the patient encounter based, at least in part, upon machine vision encounter information 102. As discussed above, mixed-media ACI device 232 (and machine vision system 100/audio recording system 104 included therein) may be configured to monitor one or more encounter participants (e.g., encounter participants 226, 228, 230) of a patient encounter.

Specifically and as will be discussed below in greater detail, machine vision system 100 (either as a stand-alone system or as a component of mixed-media ACI device 232) may be configured to detect humanoid shapes within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility). And when these humanoid shapes are detected by machine vision system 100, modular ACI system 54 and/or audio recording system 104 may be configured to utilize one or more of the discrete audio acquisition devices (e.g., audio acquisition devices 202, 204, 206, 208, 210, 212, 214, 216, 218) to form an audio recording beam (e.g., audio recording beams 220, 222, 224) that is directed toward each of the detected humanoid shapes (e.g., encounter participants 226, 228, 230).

As discussed above, ACI compute system 12 may be configured to receive machine vision encounter information 102 and audio encounter information 106 from machine vision system 100 and audio recording system 104 (respectively); and may be configured to provide visual information 110 and audio information 114 to display rendering system 108 and audio rendering system 112 (respectively). Depending upon the manner in which modular ACI system 54 (and/or mixed-media ACI device 232) is configured, ACI compute system 12 may be included within mixed-media ACI device 232 or external to mixed-media ACI device 232.

The Ambient Cooperative Intelligence Process

As discussed above, ACI compute system 12 may execute all or a portion of ambient cooperative intelligence process 10, wherein the instruction sets and subroutines of ambient cooperative intelligence process 10 (which may be stored on one or more of e.g., storage devices 16, 20, 22, 24, 26) may be executed by ACI compute system 12 and/or one or more of ACI client electronic devices 28, 30, 32, 34.

Figure 4:
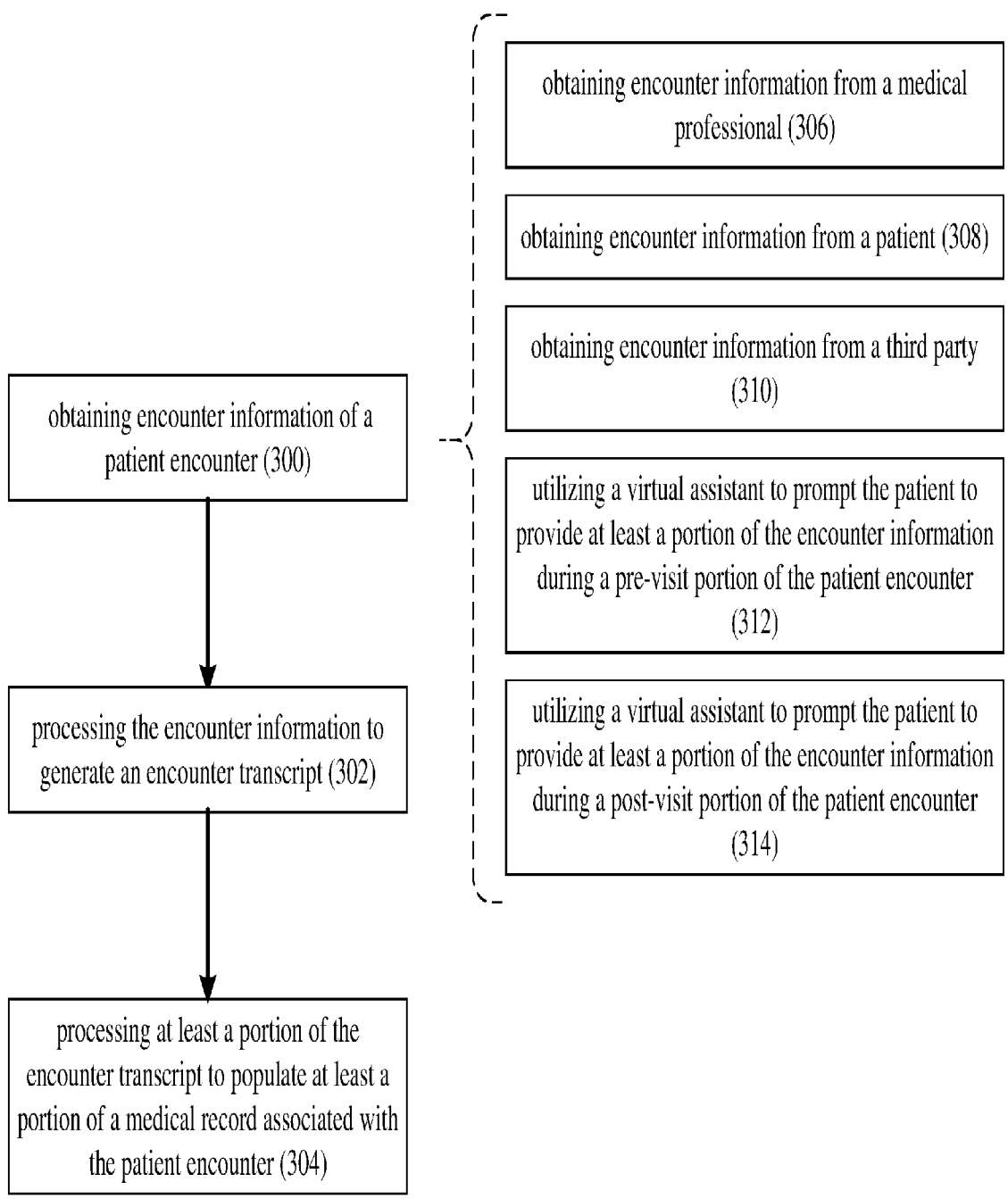
FIG. 4 is a flow chart of one implementation of the ambient cooperative intelligence process of FIG. 1.

As discussed above, ambient cooperative intelligence process 10 may be configured to automate the collection and processing of clinical encounter information to generate/store/distribute medical records. Accordingly and referring also to FIG. 4, ambient cooperative intelligence process 10 may be configured to obtain 300 encounter information (e.g., machine vision encounter information 102 and/or audio encounter information 106) of a patient encounter (e.g., a visit to a doctor's office). Ambient cooperative intelligence process 10 may further be configured to process 302 the encounter information (e.g., machine vision encounter information 102 and/or audio encounter information 106) to generate an encounter transcript (e.g., encounter transcript 234), wherein ambient cooperative intelligence process 10 may then process 304 at least a portion of the encounter transcript (e.g., encounter transcript 234) to populate at least a portion of a medical record (e.g., medical record 236) associated with the patient encounter (e.g., the visit to the doctor's office). Encounter transcript 234 and/or medical record 236 may be reviewed by a medical professional involved with the patient encounter (e.g., a visit to a doctor's office) to determine the accuracy of the same and/or make corrections to the same.

For example, a scribe involved with (or assigned to) the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, ambient cooperative intelligence process 10 may utilize these corrections for training/tuning purposes (e.g., to adjust the various profiles associated the participants of the patient encounter) to enhance the future accuracy/efficiency/performance of ambient cooperative intelligence process 10.

Alternatively/additionally, a doctor involved with the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, ambient cooperative intelligence process 10 may utilize these corrections for training/tuning purposes (e.g., to adjust the various profiles associated the participants of the patient encounter) to enhance the future accuracy/efficiency/performance of ambient cooperative intelligence process 10.

For example, assume that a patient (e.g., encounter participant 228) visits a clinical environment (e.g., a doctor's office) because they do not feel well. They have a headache, fever, chills, a cough, and some difficulty breathing. In this particular example, a monitored space (e.g., monitored space 130) within the clinical environment (e.g., the doctor's office) may be outfitted with machine vision system 100 configured to obtain machine vision encounter information 102 concerning the patient encounter (e.g., encounter participant 228 visiting the doctor's office) and audio recording system 104 configured to obtain audio encounter information 106 concerning the patient encounter (e.g., encounter participant 228 visiting the doctor's office) via one or more audio sensors (e.g., audio acquisition devices 202, 204, 206, 208, 210, 212, 214, 216, 218).

As discussed above, machine vision system 100 may include a plurality of discrete machine vision systems if the monitored space (e.g., monitored space 130) within the clinical environment (e.g., the doctor's office) is larger or a higher level of resolution is desired, wherein examples of machine vision system 100 may include but are not limited to: an RGB imaging system, an infrared imaging system, an ultraviolet imaging system, a laser imaging system, a SONAR imaging system, a RADAR imaging system, and a thermal imaging system. Accordingly and in certain instances/embodiments, machine vision system 100 may include one or more of each of an RGB imaging system, an infrared imaging system, an ultraviolet imaging system, a laser imaging system, a SONAR imaging system, a RADAR imaging system, and a thermal imaging system positioned throughout monitored space 130, wherein each of these systems may be configured to provide data (e.g., machine vision encounter information 102) to ACI compute system 12 and/or modular ACI system 54.

As also discussed above, audio recording system 104 may include a plurality of discrete audio recording systems if the monitored space (e.g., monitored space 130) within the clinical environment (e.g., the doctor's office) is larger or a higher level of resolution is desired, wherein examples of audio recording system 104 may include but are not limited to: a handheld microphone, a lapel microphone, an embedded microphone (such as those embedded within eyeglasses, smart phones, tablet computers and/or watches) and an audio recording device. Accordingly and in certain instances/embodiments, audio recording system 104 may include one or more of each of a handheld microphone, a lapel microphone, an embedded microphone (such as those embedded within eyeglasses, smart phones, tablet computers and/or watches) and an audio recording device positioned throughout monitored space 130, wherein each of these microphones/devices may be configured to provide data (e.g., audio encounter information 106) to ACI compute system 12 and/or modular ACI system 54.

Since machine vision system 100 and audio recording system 104 may be positioned throughout monitored space 130, all of the interactions between medical professionals (e.g., encounter participant 226), patients (e.g., encounter participant 228) and third parties (e.g., encounter participant 230) that occur during the patient encounter (e.g., encounter participant 228 visiting the doctor's office) within the monitored space (e.g., monitored space 130) of the clinical environment (e.g., the doctor's office) may be monitored/recorded/processed. Accordingly, a patient "check-in" area within monitored space 130 may be monitored to obtain encounter information (e.g., machine vision encounter information 102 and/or audio encounter information 106) during this pre-visit portion of the patient encounter (e.g., encounter participant 228 visiting the doctor's office). Further, various rooms within monitored space 130 may be monitored to obtain encounter information (e.g., machine vision encounter information 102 and/or audio encounter information 106) during these various portions of the patient encounter (e.g., while meeting with the doctor, while vital signs and statistics are obtained, and while imaging is performed). Further, a patient "check-out" area within monitored space 130 may be monitored to obtain encounter information (e.g., machine vision encounter information 102 and/or audio encounter information 106) during this post-visit portion of the patient encounter (e.g., encounter participant 228 visiting the doctor's office). Additionally and via machine vision encounter information 102, visual speech recognition (via visual lip reading functionality) may be utilized by ambient cooperative intelligence process 10 to further effectuate the gathering of audio encounter information 106.

Accordingly and when obtaining 300 encounter information (e.g., machine vision encounter information 102 and/or audio encounter information 106), ambient cooperative intelligence process 10 may: obtain 306 encounter information (e.g., machine vision encounter information 102 and/or audio encounter information 106) from a medical professional (e.g., encounter participant 226); obtain 308 encounter information (e.g., machine vision encounter information 102 and/or audio encounter information 106) from a patient (e.g., encounter participant 228); and/or obtain 310 encounter information (e.g., machine vision encounter information 102 and/or audio encounter information 106) from a third party (e.g., encounter participant 230). Further and when obtaining 300 encounter information (e.g., machine vision encounter information 102 and/or audio encounter information 106), ambient cooperative intelligence process 10 may obtain 300 the encounter information (e.g., machine vision encounter information 102 and/or audio encounter information 106) from previous (related or unrelated) patient encounters. For example, if the current patient encounter is actually the third visit that the patient is making concerning e.g., shortness of breath, the encounter information from the previous two visits (i.e., the previous two patient encounters) may be highly-related and may be obtained 300 by ambient cooperative intelligence process 10.

When ambient cooperative intelligence process 10 obtains 300 the encounter information, ambient cooperative intelligence process 10 may utilize 312 a virtual assistant (e.g., virtual assistant 238) to prompt the patient (e.g., encounter participant 228) to provide at least a portion of the encounter information (e.g., machine vision encounter information 102 and/or audio encounter information 106) during a pre-visit portion (e.g., a patient intake portion) of the patient encounter (e.g., encounter participant 228 visiting the doctor's office).

Further and when ambient cooperative intelligence process 10 obtains 300 encounter information, ambient cooperative intelligence process 10 may utilize 314 a virtual assistant (e.g., virtual assistant 238) to prompt the patient (e.g., encounter participant 228) to provide at least a portion of the encounter information (e.g., machine vision encounter information 102 and/or audio encounter information 106) during a post-visit portion (e.g., a patient follow-up portion) of the patient encounter (e.g., encounter participant 228 visiting the doctor's office).

Automated Transcript Generation

Ambient cooperative intelligence process 10 may be configured to process the encounter information (e.g., machine vision encounter information 102 and/or audio encounter information 106) to generate encounter transcript 234 that may be automatically formatted and punctuated.

Figure 5:
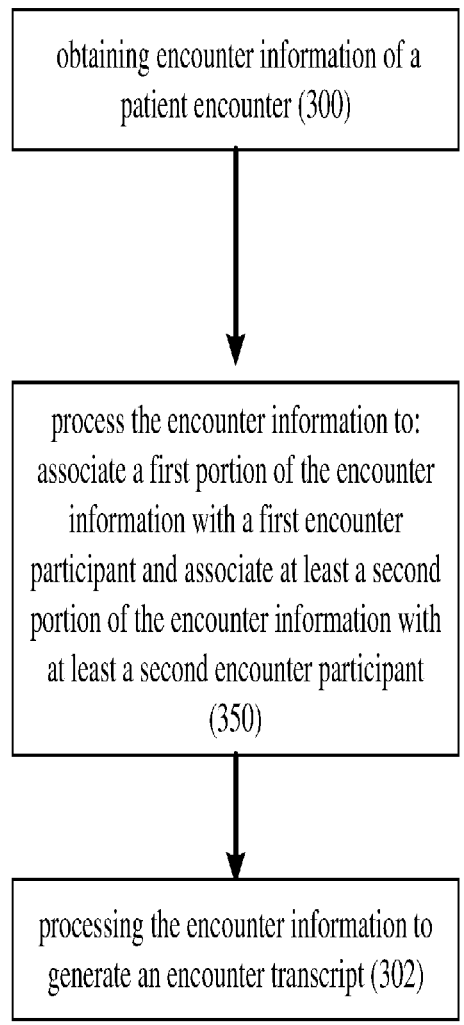
FIG. 5 is a flow chart of another implementation of the ambient cooperative intelligence process of FIG. 1.

Accordingly and referring also to FIG. 5, ambient cooperative intelligence process 10 may be configured to obtain 300 encounter information (e.g., machine vision encounter information 102 and/or audio encounter information 106) of a patient encounter (e.g., a visit to a doctor's office).

Ambient cooperative intelligence process 10 may process 350 the encounter information (e.g., machine vision encounter information 102 and/or audio encounter information 106) to: associate a first portion of the encounter information (e.g., machine vision encounter information 102 and/or audio encounter information 106) with a first encounter participant, and associate at least a second portion of the encounter information (e.g., machine vision encounter information 102 and/or audio encounter information 106) with at least a second encounter participant.

As discussed above, modular ACI system 54 may be configured to form one or more audio recording beams (e.g., audio recording beams 220, 222, 224) via the discrete audio acquisition devices (e.g., discrete audio acquisition devices 202, 204, 206, 208, 210, 212, 214, 216, 218) included within audio recording system 104, wherein modular ACI system 54 may be further configured to steer the one or more audio recording beams (e.g., audio recording beams 220, 222, 224) toward one or more encounter participants (e.g., encounter participants 226, 228, 230) of the above-described patient encounter.

Accordingly and continuing with the above-stated example, modular ACI system 54 may steer audio recording beam 220 toward encounter participant 226, may steer audio recording beam 222 toward encounter participant 228, and may steer audio recording beam 224 toward encounter participant 230. Accordingly and due to the directionality of audio recording beams 220, 222, 224, audio encounter information 106 may include three components, namely audio encounter information 106A (which is obtained via audio recording beam 220), audio encounter information 106B (which is obtained via audio recording beam 222) and audio encounter information 106C (which is obtained via audio recording beam 220).

Further and as discussed above, ACI compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, a physical events datasource, and a home healthcare datasource.

Accordingly, ambient cooperative intelligence process 10 may process 350 the encounter information (e.g., machine vision encounter information 102 and/or audio encounter information 106) to: associate a first portion (e.g., encounter information 106A) of the encounter information (e.g., audio encounter information 106) with a first encounter participant (e.g., encounter participant 226), and associate at least a second portion (e.g., encounter information 106B, 106C) of the encounter information (e.g., audio encounter information 106) with at least a second encounter participant (e.g., encounter participants 228, 230; respectively).

Further and when processing 350 the encounter information (e.g., audio encounter information 106A, 106B, 106C), ambient cooperative intelligence process 10 may compare each of audio encounter information 106A, 106B, 106C to the voice prints defined within the above-referenced voice print datasource so that the identity of encounter participants 226, 228, 230 (respectively) may be determined. Accordingly, if the voice print datasource includes a voice print that corresponds to one or more of the voice of encounter participant 226 (as heard within audio encounter information 106A), the voice of encounter participant 228 (as heard within audio encounter information 106B) or the voice of encounter participant 230 (as heard within audio encounter information 106C), the identity of one or more of encounter participants 226, 228, 230 may be defined. And in the event that a voice heard within one or more of audio encounter information 106A, audio encounter information 106B or audio encounter information 106C is unidentifiable, that one or more particular encounter participant may be defined as "Unknown Participant".

Once the voices of encounter participants 226, 228, 230 are processed 350, ambient cooperative intelligence process 10 may generate 302 an encounter transcript (e.g., encounter transcript 234) based, at least in part, upon the first portion of the encounter information (e.g., audio encounter information 106A) and the at least a second portion of the encounter information (e.g., audio encounter information 106B. 106C).

Automated Role Assignment

Ambient cooperative intelligence process 10 may be configured to automatically define roles for the encounter participants (e.g., encounter participants 226, 228, 230) in the patient encounter (e.g., a visit to a doctor's office).

Figure 6:
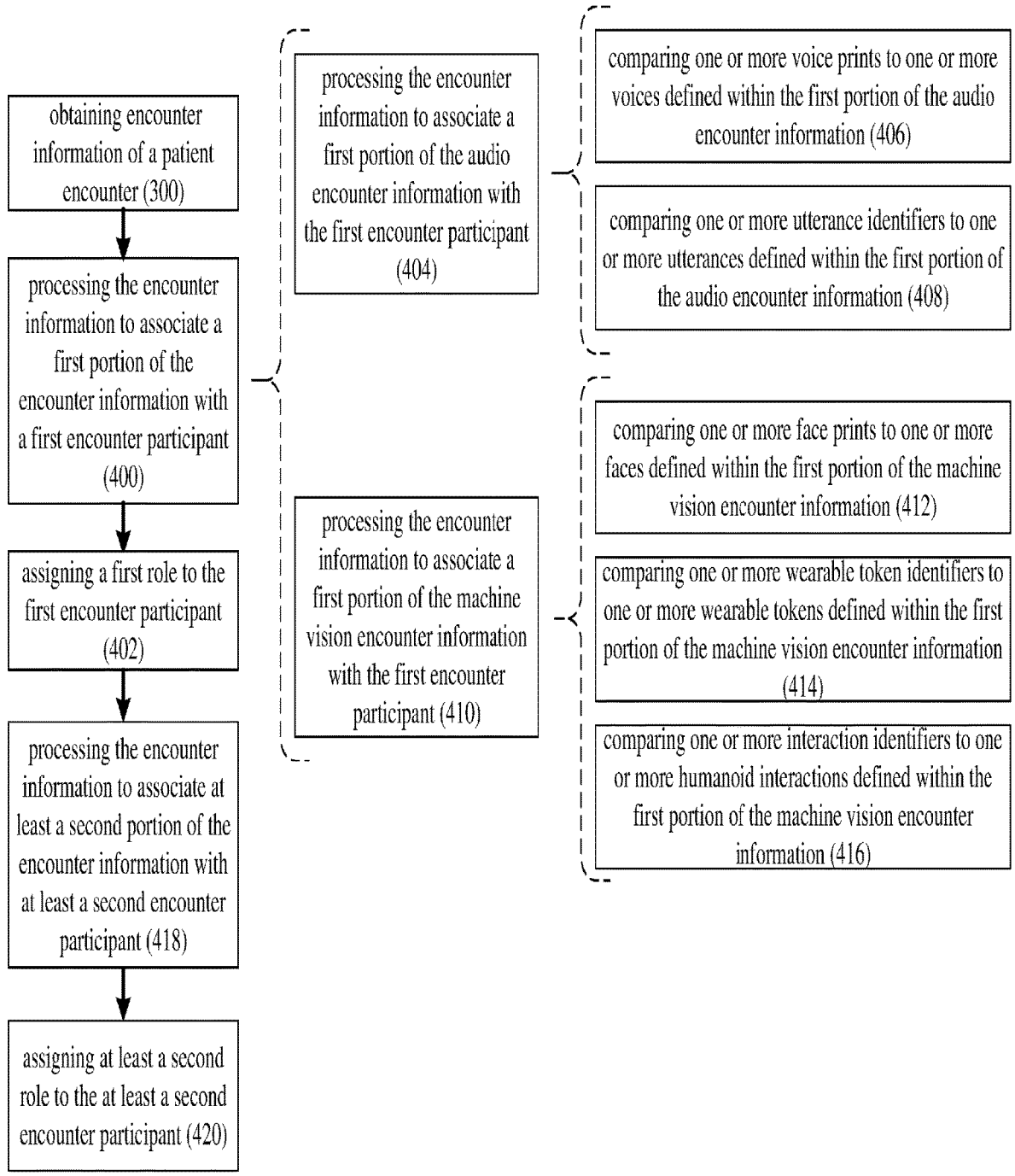
FIG. 6 is a flow chart of another implementation of the ambient cooperative intelligence process of FIG. 1.

Accordingly and referring also to FIG. 6, ambient cooperative intelligence process 10 may be configured to obtain 300 encounter information (e.g., machine vision encounter information 102 and/or audio encounter information 106) of a patient encounter (e.g., a visit to a doctor's office).

Ambient cooperative intelligence process 10 may then process 400 the encounter information (e.g., machine vision encounter information 102 and/or audio encounter information 106) to associate a first portion of the encounter information with a first encounter participant (e.g., encounter participant 226) and assign 402 a first role to the first encounter participant (e.g., encounter participant 226).

When processing 400 the encounter information (e.g., machine vision encounter information 102 and/or audio encounter information 106) to associate the first portion of the encounter information with the first encounter participant (e.g., encounter participant 226), ambient cooperative intelligence process 10 may process 404 the encounter information (e.g., machine vision encounter information 102 and/or audio encounter information 106) to associate a first portion of the audio encounter information (e.g., audio encounter information 106A) with the first encounter participant (e.g., encounter participant 226).

Specifically and when processing 404 the encounter information (e.g., machine vision encounter information 102 and/or audio encounter information 106) to associate the first portion of the audio encounter information (e.g., audio encounter information 106A) with the first encounter participant (e.g., encounter participant 226), ambient cooperative intelligence process 10 may compare 406 one or more voice prints (defined within voice print datasource) to one or more voices defined within the first portion of the audio encounter information (e.g., audio encounter information 106A); and may compare 408 one or more utterance identifiers (defined within utterance datasource) to one or more utterances defined within the first portion of the audio encounter information (e.g., audio encounter information 106A); wherein comparisons 406, 408 may allow ambient cooperative intelligence process 10 to assign 402 a first role to the first encounter participant (e.g., encounter participant 226). For example, if the identity of encounter participant 226 can be defined via voice prints, a role for encounter participant 226 may be assigned 402 if that identity defined is associated with a role (e.g., the identity defined for encounter participant 226 is Doctor Susan Jones). Further, if an utterance made by encounter participant 226 is "I am Doctor Susan Jones", this utterance may allow a role for encounter participant 226 to be assigned 402.

When processing 400 the encounter information (e.g., machine vision encounter information 102 and/or audio encounter information 106) to associate the first portion of the encounter information with the first encounter participant (e.g., encounter participant 226), ambient cooperative intelligence process 10 may process 410 the encounter information (e.g., machine vision encounter information 102 and/or audio encounter information 106) to associate a first portion of the machine vision encounter information (e.g., machine vision encounter information 102A) with the first encounter participant (e.g., encounter participant 226).

Specifically and when processing 410 the encounter information (e.g., machine vision encounter information 102 and/or audio encounter information 106) to associate the first portion of the machine vision encounter information (e.g., machine vision encounter information 102A) with the first encounter participant (e.g., encounter participant 226), ambient cooperative intelligence process 10 may compare 412 one or more face prints (defined within face print datasource) to one or more faces defined within the first portion of the machine vision encounter information (e.g., machine vision encounter information 102A); compare 414 one or more wearable token identifiers (defined within wearable token identifier datasource) to one or more wearable tokens defined within the first portion of the machine vision encounter information (e.g., machine vision encounter information 102A); and compare 416 one or more interaction identifiers (defined within interaction identifier datasource) to one or more humanoid interactions defined within the first portion of the machine vision encounter information (e.g., machine vision encounter information 102A); wherein comparisons 412, 414, 416 may allow ambient cooperative intelligence process 10 to assign 402 a first role to the first encounter participant (e.g., encounter participant 226). For example, if the identity of encounter participant 226 can be defined via face prints, a role for encounter participant 226 may be assigned 402 if that identity defined is associated with a role (e.g., the identity defined for encounter participant 226 is Doctor Susan Jones). Further, if a wearable token worn by encounter participant 226 can be identified as a wearable token assigned to Doctor Susan Jones, a role for encounter participant 226 may be assigned 402. Additionally, if an interaction made by encounter participant 226 corresponds to the type of interaction that is made by a doctor, the existence of this interaction may allow a role for encounter participant 226 to be assigned 402.

Examples of such wearable tokens may include but are not limited to wearable devices that may be worn by the medical professionals when they are within monitored space 130 (or after they leave monitored space 130). For example, these wearable tokens may be worn by medical professionals when e.g., they are moving between monitored rooms within monitored space 130, travelling to and/or from monitored space 130, and/or outside of monitored space 130 (e.g., at home).

Additionally, ambient cooperative intelligence process 10 may process 418 the encounter information (e.g., machine vision encounter information 102 and/or audio encounter information 106) to associate at least a second portion of the encounter information with at least a second encounter participant; and may assign 420 at least a second role to the at least a second encounter participant.

Specifically, ambient cooperative intelligence process 10 may process 418 the encounter information (e.g., machine vision encounter information 102 and/or audio encounter information 106) to associate at least a second portion of the encounter information with at least a second encounter participant. For example, ambient cooperative intelligence process 10 may process 418 the encounter information (e.g., machine vision encounter information 102 and/or audio encounter information 106) to associate audio encounter information 106B and machine vision encounter information 102B with encounter participant 228 and may associate audio encounter information 106C and machine vision encounter information 102C with encounter participant 230.

Further, ambient cooperative intelligence process 10 may assign 420 at least a second role to the at least a second encounter participant. For example, ambient cooperative intelligence process 10 may assign 420 a role to encounter participants 228, 230.

Automated Movement Tracking

Ambient cooperative intelligence process 10 may be configured to track the movement and/or interaction of humanoid shapes within the monitored space (e.g., monitored space 130) during the patient encounter (e.g., a visit to a doctor's office) so that e.g., the ambient cooperative intelligence process 10 knows when encounter participants (e.g., one or more of encounter participants 226, 228, 230) enter, exit or cross paths within monitored space 130.

Figure 7:
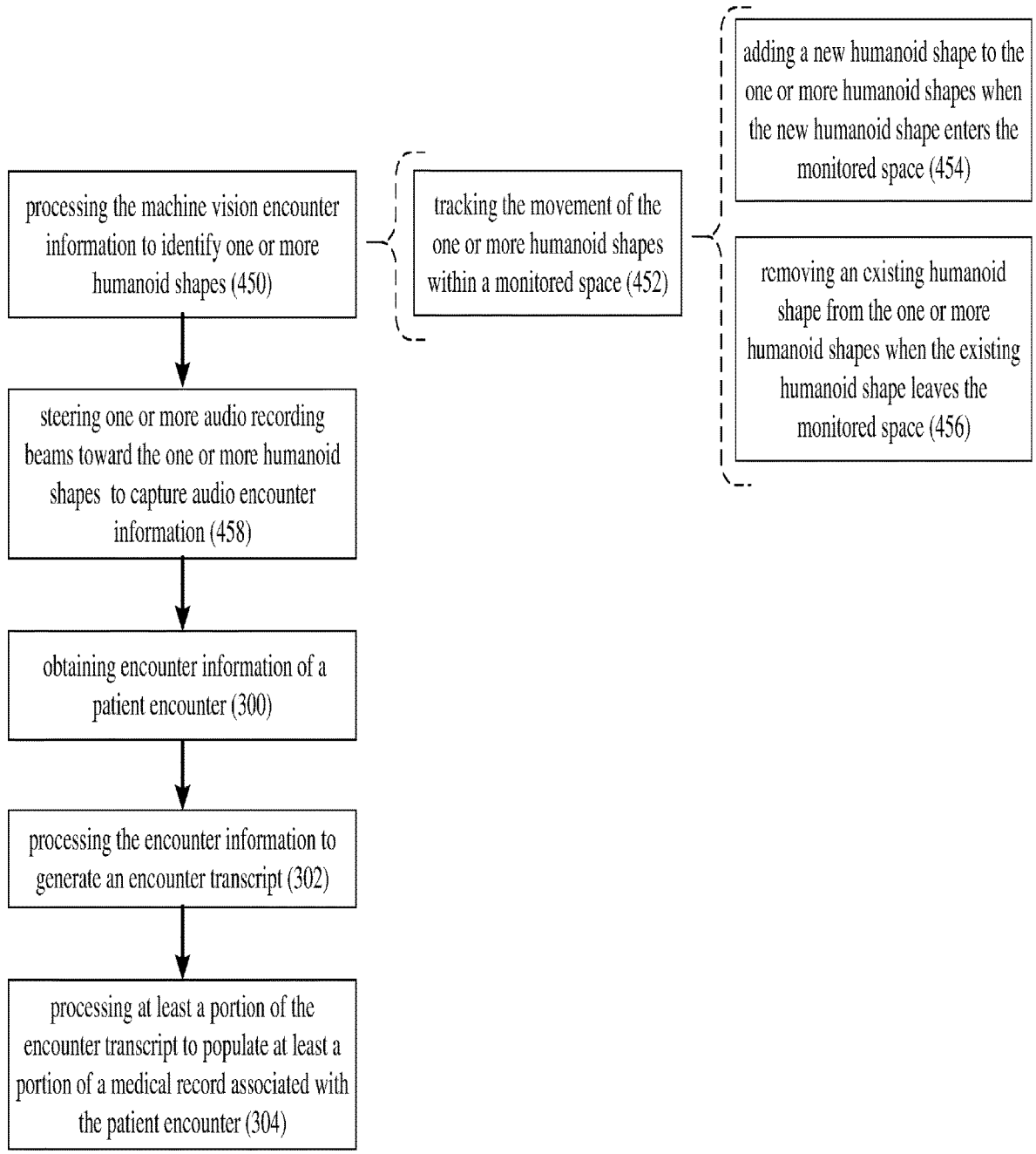
FIG. 7 is a flow chart of another implementation of the ambient cooperative intelligence process of FIG. 1.

Accordingly and referring also to FIG. 7, ambient cooperative intelligence process 10 may process 450 the machine vision encounter information (e.g., machine vision encounter information 102) to identify one or more humanoid shapes. As discussed above, examples of machine vision system 100 generally (and ACI client electronic device 34 specifically) may include but are not limited to one or more of an RGB imaging system, an infrared imaging system, an ultraviolet imaging system, a laser imaging system, a SONAR imaging system, a RADAR imaging system, and a thermal imaging system).

When ACI client electronic device 34 includes a visible light imaging system (e.g., an RGB imaging system), ACI client electronic device 34 may be configured to monitor various objects within monitored space 130 by recording motion video in the visible light spectrum of these various objects. When ACI client electronic device 34 includes an invisible light imaging system (e.g., a laser imaging system, an infrared imaging system and/or an ultraviolet imaging system), ACI client electronic device 34 may be configured to monitor various objects within monitored space 130 by recording motion video in the invisible light spectrum of these various objects. When ACI client electronic device 34 includes an X-ray imaging system, ACI client electronic device 34 may be configured to monitor various objects within monitored space 130 by recording energy in the X-ray spectrum of these various objects. When ACI client electronic device 34 includes a SONAR imaging system, ACI client electronic device 34 may be configured to monitor various objects within monitored space 130 by transmitting soundwaves that may be reflected off of these various objects. When ACI client electronic device 34 includes a RADAR imaging system, ACI client electronic device 34 may be configured to monitor various objects within monitored space 130 by transmitting radio waves that may be reflected off of these various objects. When ACI client electronic device 34 includes a thermal imaging system, ACI client electronic device 34 may be configured to monitor various objects within monitored space 130 by tracking the thermal energy of these various objects.

As discussed above, ACI compute system 12 may be configured to access one or more datasources 118 (e.g., plurality of individual datasources 120, 122, 124, 126, 128), wherein examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, a physical events datasource, and a home healthcare datasource.

Accordingly and when processing 450 the machine vision encounter information (e.g., machine vision encounter information 102) to identify one or more humanoid shapes, ambient cooperative intelligence process 10 may be configured to compare the humanoid shapes defined within one or more datasources 118 to potential humanoid shapes within the machine vision encounter information (e.g., machine vision encounter information 102).

When processing 450 the machine vision encounter information (e.g., machine vision encounter information 102) to identify one or more humanoid shapes, ambient cooperative intelligence process 10 may track 452 the movement of the one or more humanoid shapes within the monitored space (e.g., monitored space 130). For example and when tracking 452 the movement of the one or more humanoid shapes within monitored space 130, ambient cooperative intelligence process 10 may add 454 a new humanoid shape to the one or more humanoid shapes when the new humanoid shape enters the monitored space (e.g., monitored space 130) and/or may remove 456 an existing humanoid shape from the one or more humanoid shapes when the existing humanoid shape leaves the monitored space (e.g., monitored space 130).

For example, assume that a lab technician (e.g., encounter participant 242) temporarily enters monitored space 130 to chat with encounter participant 230. Accordingly, ambient cooperative intelligence process 10 may add 454 encounter participant 242 to the one or more humanoid shapes being tracked 452 when the new humanoid shape (i.e., encounter participant 242) enters monitored space 130. Further, assume that the lab technician (e.g., encounter participant 242) leaves monitored space 130 after chatting with encounter participant 230. Therefore, ambient cooperative intelligence process 10 may remove 456 encounter participant 242 from the one or more humanoid shapes being tracked 452 when the humanoid shape (i.e., encounter participant 242) leaves monitored space 130.

Also and when tracking 452 the movement of the one or more humanoid shapes within monitored space 130, ambient cooperative intelligence process 10 may monitor the trajectories of the various humanoid shapes within monitored space 130. Accordingly, assume that when leaving monitored space 130, encounter participant 242 walks in front of (or behind) encounter participant 226. As ambient cooperative intelligence process 10 is monitoring the trajectories of (in this example) encounter participant 242 (who is e.g., moving from left to right) and encounter participant 226 (who is e.g., stationary), when encounter participant 242 passes in front of (or behind) encounter participant 226, the identities of these two humanoid shapes may not be confused by ambient cooperative intelligence process 10.

Ambient cooperative intelligence process 10 may be configured to obtain 300 the encounter information of the patient encounter (e.g., a visit to a doctor's office), which may include machine vision encounter information 102 (in the manner described above) and/or audio encounter information 106.

Ambient cooperative intelligence process 10 may steer 458 one or more audio recording beams (e.g., audio recording beams 220, 222, 224) toward the one or more humanoid shapes (e.g., encounter participants 226, 228, 230) to capture audio encounter information (e.g., audio encounter information 106), wherein audio encounter information 106 may be included within the encounter information (e.g., machine vision encounter information 102 and/or audio encounter information 106).

Specifically and as discussed above, ambient cooperative intelligence process 10 (via modular ACI system 54 and/or audio recording system 104) may utilize one or more of the discrete audio acquisition devices (e.g., audio acquisition devices 202, 204, 206, 208, 210, 212, 214, 216, 218) to form an audio recording beam. For example, modular ACI system 54 and/or audio recording system 104 may be configured to utilize various audio acquisition devices to form audio recording beam 220, thus enabling the capturing of audio (e.g., speech) produced by encounter participant 226 (as audio recording beam 220 is pointed to (i.e., directed toward) encounter participant 226). Additionally, modular ACI system 54 and/or audio recording system 104 may be configured to utilize various audio acquisition devices to form audio recording beam 222, thus enabling the capturing of audio (e.g., speech) produced by encounter participant 228 (as audio recording beam 222 is pointed to (i.e., directed toward) encounter participant 228). Additionally, modular ACI system 54 and/or audio recording system 104 may be configured to utilize various audio acquisition devices to form audio recording beam 224, thus enabling the capturing of audio (e.g., speech) produced by encounter participant 230 (as audio recording beam 224 is pointed to (i.e., directed toward) encounter participant 230).

Once obtained, ambient cooperative intelligence process 10 may process 302 the encounter information (e.g., machine vision encounter information 102 and/or audio encounter information 106) to generate encounter transcript 234 and may process 304 at least a portion of encounter transcript 234 to populate at least a portion of a medical record (e.g., medical record 236) associated with the patient encounter (e.g., a visit to a doctor's office).

Processing of Verbal Commands:

As discussed above and as shown in FIG. 2, modular ACI system 54 may be configured to automate cooperative intelligence, wherein modular ACI system 54 may include: machine vision system 100 configured to obtain machine vision encounter information 102 concerning a patient encounter; audio recording system 104 configured to obtain audio encounter information 106 concerning the patient encounter; and a compute system (e.g., ACI compute system 12) configured to receive machine vision encounter information 102 and audio encounter information 106 from machine vision system 100 and audio recording system 104 (respectively).

Ambient cooperative intelligence process 10 may be configured to receive and process verbal commands from a requester (e.g., encounter participants 226) via a virtual assistant (e.g., virtual assistant 238). For example, encounter participant 226 may issue a verbal command to the ACI platform (e.g., modular ACI system 54) such as "Hey Dragon, please display the chest X-Ray for encounter participant XXX". The "Hey Dragon" portion of this verbal command may be a wake-up word/phrase. As is known in the art, a wake-up word/phrase is a particular word (or string of words) that, when detected by (in this example) ambient cooperative intelligence process 10, may result in ambient cooperative intelligence process 10 processing the word/phrase that follows the wake-up word/phrase (namely the system-directed command).

Ambient cooperative intelligence process 10 may utilize a voice print (e.g., defined within one or more datasources 118) to authenticate that the requester (e.g., encounter participant 226) has the authority to issue such a command (e.g., "Hey Dragon, please display the chest X-Ray for encounter participant XXX"). For example, the voice of the requester (e.g., encounter participant 226) may be compared to the voice prints defined within a voice print datasource to determine if a match occurs.

Continuing with the above-stated example, encounter participant 226 may issue the verbal command to modular ACI system 54 (namely "Hey Dragon, please display the chest X-Ray for encounter participant XXX"). Upon detecting the wake-up word/phrase (namely "Hey Dragon"), ambient cooperative intelligence process 10 may process the system-directed command following the wake-up word/phrase (namely " . . . please display the chest X-Ray for encounter participant XXX"). Accordingly, the wake-up word/phrase (namely "Hey Dragon") may precede and trigger the processing of the system-directed command (namely " . . . please display the chest X-Ray for encounter participant XXX"). Therefore and with respect to a virtual assistant encounter, the virtual assistant (e.g., virtual assistant 238) may become active and may listen for virtual assistant commands starting with a wake-up word/phrase (e.g., 'Hey Dragon, . . . "), wherein speech segments starting with the wake-up word/phrase (e.g., 'Hey Dragon, . . . ") may be processed by ambient cooperative intelligence process 10.

Figure 8:
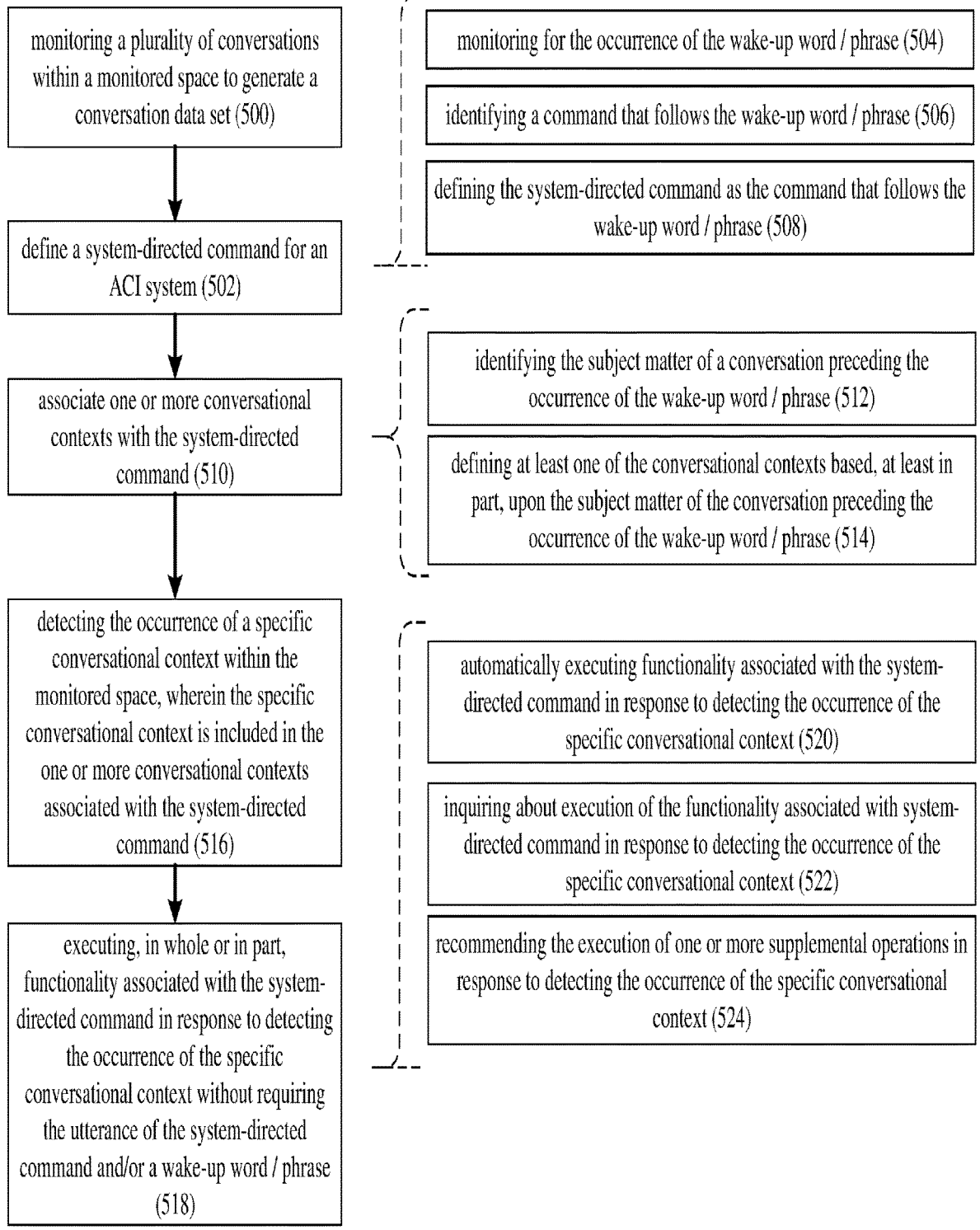
FIG. 8 is a flow chart of another implementation of the ambient cooperative intelligence process of FIG. 1.

Associating Context with Verbal Commands:

As discussed above and referring also to FIG. 8, ambient cooperative intelligence process 10 may monitor 500 a plurality of conversations within a monitored space (e.g., monitored space 130) to generate conversation data set 132. Further and as discussed above, modular ACI system 54 may include: machine vision system 100 configured to obtain machine vision encounter information 102 concerning a patient encounter; audio recording system 104 configured to obtain audio encounter information 106 concerning the patient encounter; and a compute system (e.g., ACI compute system 12) configured to receive machine vision encounter information 102 and audio encounter information 106 from machine vision system 100 and audio recording system 104 (respectively).

Accordingly, ambient cooperative intelligence process 10 may monitor 500 the conversations that occur within monitored space 130 and obtain audio encounter information 106 for each of these conversations, thus resulting in the generation of conversation data set 132. Accordingly, as the period of time that ambient cooperative intelligence process 10 monitors 500 the conversations within monitored space 130 increases, so does the size and completeness of conversation data set 132.

Once conversation data set 132 is generated, ambient cooperative intelligence process 10 may process conversation data set 132 using machine learning to:
define 502 a system-directed command for an ACI system (e.g., modular ACI system 54), and
associate 504 one or more conversational contexts with the system-directed command;

As is known in the art, machine learning (ML) is the study of computer algorithms that improve automatically through experience, wherein machine learning is seen as a subset of artificial intelligence. Machine learning algorithms build a model based on sample data, known as "training data", in order to make predictions or decisions without being explicitly programmed to do so. As will be discussed below, this "training data" is conversation data set 132, which will be processed using machine learning by ambient cooperative intelligence process 10

As discussed above, ambient cooperative intelligence process 10 may define 502 a system-directed command for an ACI system (e.g., modular ACI system 54), wherein (as discussed above) modular ACI system 54 is configured to monitor conversations (e.g., between encounter participant 226 and encounter participant XXX) within monitored space 130. Specifically, since system-directed commands (e.g., " . . . please display the chest X-Ray for encounter participant XXX") typically follow a wake-up word/phrase (e.g., "Hey Dragon"), ambient cooperative intelligence process 10 may define 502 system-directed commands by monitoring for the occurrence of the wake-up word/phrase (e.g., "Hey Dragon") and defining 502 a system-directed command as the command that follows the wake-up word/phrase (e.g., "Hey Dragon").

Specifically and when defining 502 a system-directed command for an ACI system (e.g., modular ACI system 54), ambient cooperative intelligence process 10 may:
monitor 504 for the occurrence of a wake-up word/phrase (e.g., "Hey Dragon");
identify 506 a command that follows the wake-up word/phrase (e.g., "Hey Dragon"); and define 508 the system-directed command as the command that follows the wake-up word/phrase (e.g., "Hey Dragon").

For example and when defining 502 a system-directed command for modular ACI system 54, ambient cooperative intelligence process 10 may process (using machine learning) conversation data set 132 to monitor 504 for the occurrence of a wake-up word/phrase. Accordingly and if encounter participant 226 says "Hey Dragon, please display the chest X-Ray for encounter participant XXX", ambient cooperative intelligence process 10 may identify 506 and define 508 the command (namely " . . . please display the chest X-Ray for encounter participant XXX") that follows the wake-up word/phrase (e.g., "Hey Dragon") as a system-directed command.

As another example and when processing (using machine learning) conversation data set 132 to monitor 504 for the occurrence of a wake-up word/phrase, if encounter participant 226 says "Hey Dragon, please schedule blood work for encounter participant XXX", ambient cooperative intelligence process 10 may identify 506 and define 508 the command (namely " . . . please schedule blood work for encounter participant XXX") that follows the wake-up word/phrase (e.g., "Hey Dragon") as a system-directed command.

And as another example and when processing (using machine learning) conversation data set 132 to monitor 504 for the occurrence of a wake-up word/phrase, if encounter participant 226 says "Hey Dragon, please schedule a follow up visit for encounter participant XXX", ambient cooperative intelligence process 10 may identify 506 and define 508 the command (namely " . . . please schedule a follow up visit for encounter participant XXX") that follows the wake-up word/phrase (e.g., "Hey Dragon") as a system-directed command.

As could be imagined, as ambient cooperative intelligence process 10 processes (using machine learning) the conversations defined within conversation data set 132, the quantity of system-directed commands defined 502 by ambient cooperative intelligence process 10 may greatly increase. Accordingly, ambient cooperative intelligence process 10 may be configured to store these system-directed commands (in this example, " . . . please display the chest X-Ray for encounter participant XXX"; " . . . please schedule blood work for encounter participant XXX"; and " . . . please schedule a follow up visit for encounter participant XXX") within datastore 134, an example of which may include but is not limited to a database.

Ambient cooperative intelligence process 10 may associate 510 one or more conversational contexts with the system-directed command. For example and referring specifically to the system-directed command " . . . please display the chest X-Ray for encounter participant XXX" defined 502 by ambient cooperative intelligence process 10, ambient cooperative intelligence process 10 may associate 510 conversational contexts with the system-directed command (e.g., " . . . please display the chest X-Ray for encounter participant XXX") by monitoring the conversation proximate the system-directed command.

For example and when associating 510 one or more conversational contexts with the system-directed command (e.g., " . . . please display the chest X-Ray for encounter participant XXX"), ambient cooperative intelligence process 10 may:

identify 512 the subject matter of the conversation preceding the occurrence of the wake-up word/phrase (e.g., "Hey Dragon"); and define 514 at least one of the conversational contexts based, at least in part, upon the subject matter of the conversation preceding the occurrence of the wake-up word/phrase (e.g., "Hey Dragon").

As discussed above, ambient cooperative intelligence process 10 may be configured to monitor 500 a plurality of conversations within a monitored space (e.g., monitored space 130) to generate conversation data set 132, thus enabling ambient cooperative intelligence process 10 to identify 512 the subject matter of the conversation preceding the occurrence of the wake-up word/phrase (e.g., "Hey Dragon") and define 514 at least one of the conversational contexts based, at least in part, upon the subject matter of the conversation preceding the occurrence of the wake-up word/phrase (e.g., "Hey Dragon").

For example, assume that prior to encounter participant 226 saying "Hey Dragon, please display the chest X-Ray for encounter participant XXX", the subject matter of the conversation between encounter participants 226, XXX concerned the breathing difficulties and/or respiratory issues of encounter participant XXX.

For example, the conversation between encounter participants 226, XXX may have concerned:

encounter participant XXX experiencing shortness of breath when climbing stairs;

encounter participant XXX getting light-headed when exercising;

encounter participant XXX having had pneumonia on one or more occasions; and/or encounter participant XXX having been diagnosed with COPD.

Accordingly, ambient cooperative intelligence process 10 may identify 512 the subject matter of the conversation preceding the occurrence of the wake-up word/phrase (e.g., "Hey Dragon") as the breathing difficulties and/or respiratory issues of encounter participant XXX. Accordingly and once the subject matter is identified 512, ambient cooperative intelligence process 10 may define 514 at least one of the conversational contexts based, at least in part, upon the subject matter of the conversation preceding the occurrence of the wake-up word/phrase (e.g., "Hey Dragon").

As discussed above, the subject matter of the conversation between encounter participants 226, XXX concerned the breathing difficulties and/or respiratory issues of encounter participant XXX. Accordingly, ambient cooperative intelligence process 10 may associate 510 conversational contexts (e.g., breathing difficulties; respiratory issues) with the system-directed command (e.g., " . . . please display the chest X-Ray for encounter participant XXX").

While the above discussion may seem to imply some predefined ontology/feature space into which contexts are mapped via some predefined classifier, this is for simplified illustrative purposes only and is not intended to be a limitation of this disclosure. For example and when ambient cooperative intelligence process 10 associates 510 conversational contexts with system-directed commands, ambient cooperative intelligence process 10 may use a data-driven machine learning approach, which leverages the supervision provided by explicit wake-up-word use to accumulate large pairs of context (e.g., conversation to that point and encounter metadata) and associated triggered commands. For example and while the above discussion concerns the command embodiments themselves (e.g., " . . . please display the chest X-Ray for encounter participant XXX"; " . . . please schedule blood work for encounter participant XXX"; and " . . . please schedule a follow up visit for encounter participant XXX"), this is for the purpose of simplified illustration. Specifically and when associating 510 conversational contexts with system-directed commands, ambient cooperative intelligence process 10 may utilize the sematic distillation of these commands (e.g., "displayImage (modality=xray, part=chest)") that are provided by natural language understanding and/or artificial intelligence. Such sematic distillation of these commands may be used as the basis for training a deep learning-based implicit (non-verbalized) command detector that may be part of the training process and may learn an appropriate latent feature representation and corresponding feature weights.

As could be imagined, it is foreseeable that encounter participant 226 may issue the same (or similar) system-directed commands (e.g., " . . . please display the chest X-Ray . . . ") when interacting with their other patients. Accordingly and when associating 508 one or more conversational contexts with the system-directed command (e.g., " . . . please display the chest X-Ray . . . "), ambient cooperative intelligence process 10 may consider all interactions between encounter participant 226 and all of these other patients. Further, it is foreseeable that other medical professionals practicing within monitored space 130 may issue the same (or similar) system-directed commands (e.g., " . . . please display the chest X-Ray . . . ") when interacting with their patients. Accordingly and when associating 510 one or more conversational contexts with the system-directed command (e.g., " . . . please display the chest X-Ray . . . "), ambient cooperative intelligence process 10 may consider all interactions between these other medical professionals practicing within monitored space 130 and their patients.

Accordingly, ambient cooperative intelligence process 10 may be configured to store the one or more conversational contexts (e.g., breathing difficulties; respiratory issues) associated 510 with the system-directed commands (namely " . . . please display the chest X-Ray for encounter participant XXX") within datastore 134 (e.g., a database).

Therefore, ambient cooperative intelligence process 10 may define 502 (e.g., within datastore 134) a plurality of system-directed commands. Examples of such system-directed commands may include but are not limited to: " . . . please display the chest X-Ray for encounter participant XXX"; " . . . please schedule blood work for encounter participant XXX; and " . . . please schedule a follow up visit for encounter participant XXX"). And for each of these system-directed commands, ambient cooperative intelligence process 10 may associate 510 one or more conversational contexts, wherein these conversational contexts may define the subject matter of the conversation prior to the utterance of the associated system-directed commands. For example and with respect to the system-directed command " . . . please display the chest X-Ray for encounter participant XXX", the associated 510 conversational contexts may include two conversational contexts (e.g., breathing difficulties; respiratory issues).

As will be discussed below in greater detail, ambient cooperative intelligence process 10 may monitor conversations within monitored space 130 to determine if the subject matter of such conversations aligns with any of the conversational contexts defined within datastore 134 (e.g., a database). In the event that such a match occurs, ambient cooperative intelligence process 10 may effectuate functionality of the associated system-directed command.

For example, ambient cooperative intelligence process 10 may detect 516 the occurrence of a specific conversational context within the monitored space (e.g., monitored space 130), wherein this specific conversational context may be included in the one or more conversational contexts associated 510 with the system-directed command. For example, ambient cooperative intelligence process 10 may monitor the conversations within monitored space 130 to detect 516 the occurrence of a specific conversational context (e.g., breathing difficulties; respiratory issues) within the monitored space (e.g., monitored space 130).

Specifically and upon detecting 516 the occurrence of a specific conversational context within the monitored space (e.g., monitored space 130), such conversational context may be processed by ambient cooperative intelligence process 10 to yield a confidence level with respect to each potential system-directed command. As will be discussed below, if this confidence level exceeds a certain confidence threshold, functionality associated with the corresponding system-directed command may be executed (possibly only after explicit confirmation). This confidence threshold may be modified (e.g., per physician or per facility) so as to adjust the aggressiveness with which proactive actions are taken by ambient cooperative intelligence process 10.

For example and in response to detecting 516 the occurrence of the specific conversational context (e.g., breathing difficulties; respiratory issues), ambient cooperative intelligence process 10 may execute 518, in whole or in part, functionality associated with the system-directed command (e.g., " . . . please display the chest X-Ray for encounter participant XXX") without requiring the utterance of the system-directed command and/or a wake-up word/phrase.

The manner in which ambient cooperative intelligence process 10 executes 518 functionality associated with the system-directed command (e.g., " . . . please display the chest X-Ray for encounter participant XXX") without requiring the utterance of the system-directed command and/or a wake-up word/phrase may vary depending upon the confidence level of the relationship between the detected 516 conversational context and the associated 510 system-directed command.

For example and when executing 518, in whole or in part, functionality associated with the system-directed command (e.g., " . . . please display the chest X-Ray for encounter participant XXX") in response to detecting 516 the occurrence of the specific conversational context (e.g., breathing difficulties; respiratory issues), ambient cooperative intelligence process 10 may automatically execute 520 functionality associated with the system-directed command (e.g., " . . . please display the chest X-Ray for encounter participant XXX") in response to detecting 516 the occurrence of the specific conversational context (e.g., breathing difficulties; respiratory issues).

Specifically, it is foreseeable that certain relationships may have a very high confidence level. For example, if the specific conversational context detected 516 is only associated with a single system-directed command, such a relationship may have a very high confidence level and may result in ambient cooperative intelligence process 10 automatically executing 520 functionality associated with the system-directed command (e.g., " . . . please display the chest X-Ray for encounter participant XXX") when the specific conversational context (e.g., breathing difficulties; respiratory issues) is detected 516. An example of such a high confidence relationship may be the situation in which >95% of the time that the conversational context "breathing difficulties" and/or "respiratory issues" is detected 516, the encounter participant (e.g., encounter participant 226) subsequently issued the system-directed command of " . . . please display the chest X-Ray for encounter participant XXX". Accordingly and in such a situation, ambient cooperative intelligence process 10 may automatically execute 520 functionality associated with the system-directed command (e.g., " . . . please display the chest X-Ray for encounter participant XXX") and e.g., render chest X-Ray 136 for encounter participant XXX on display device 32 (e.g., a tablet computer, a computer monitor, and a smart television).

Further and when executing 518, in whole or in part, functionality associated with the system-directed command (e.g., " . . . please display the chest X-Ray for encounter participant XXX") in response to detecting 516 the occurrence of the specific conversational context (e.g., breathing difficulties; respiratory issues), ambient cooperative intelligence process 10 may inquire 522 about execution of functionality associated with the system-directed command (e.g., " . . . please display the chest X-Ray for encounter participant XXX") in response to detecting 516 the occurrence of the specific conversational context (e.g., breathing difficulties; respiratory issues).

Specifically, it is foreseeable that certain relationships may have a lower confidence level. For example, if the specific conversational context detected 516 is associated with multiple system-directed command, such a relationship may have a lower confidence level and may result in ambient cooperative intelligence process 10 inquiring 522 about execution of functionality associated with the system-directed command (e.g., " . . . please display the chest X-Ray for encounter participant XXX") when the specific conversational context (e.g., breathing difficulties; respiratory issues) is detected 516. An example of such a lower confidence relationship may be the situation in which 72% of the time that the conversational context "breathing difficulties" and/or "respiratory issues" is detected 516, the encounter participant (e.g., encounter participant 226) subsequently issued the system-directed command of " . . . please display the chest X-Ray for encounter participant XXX"; wherein the other 28% of the time that the conversational context "breathing difficulties" and/or "respiratory issues" is detected 516, the encounter participant (e.g., encounter participant 226) did not subsequently issue the system-directed command of " . . . please display the chest X-Ray for encounter participant XXX". Accordingly and in such a situation, ambient cooperative intelligence process 10 may inquire 522 about execution of functionality associated with the system-directed command (e.g., " . . . please display the chest X-Ray for encounter participant XXX"). For example, ambient cooperative intelligence process 10 may ask (e.g., audibly and/or visually) if encounter participant 226 wishes to display the chest X-Ray for encounter participant XXX. If confirmed, ambient cooperative intelligence process 10 may render chest X-Ray 136 for encounter participant XXX on display device 32 (e.g., a tablet computer, a computer monitor, and a smart television).

As discussed above, ambient cooperative intelligence process 10 may process the detected conversational context to yield a confidence level with respect to each potential system-directed command. Further and as discussed above, wake-up word/phrase driven capabilities may be used by ambient cooperative intelligence process 10 to derive training data (at scale) to power AI/ML learning models that may enable less intrusive and burdensome virtual assistant (e.g., virtual assistant 238) capabilities.

Specifically:
[(the conversation up to point of wake-up word/phrase & encounter metadata), +the command following the wake-up word/phrase] pairs may be used to learn to classify utterances (in context) into those directed to the virtual assistant (e.g., virtual assistant 238) versus the patient or other encounter participants, obviating the need to explicitly use a wake-up word/phrase for system-directed commands.

[(conversation up to point of wake-up word/phrase & encounter metadata), +the virtual assistant/natural language understanding command following wake-up word/phrase] pairs may be used for learn to classify contexts into those which should trigger a particular system-directed command invocation, thus anticipating the physician's needs and obviating the requirement to even have to utter the system-directed command to ambient cooperative intelligence process 10.

Further, contexts not followed by explicit system-directed commands may provide negative (and unlabeled) examples for classifier training (wherein the proportion of positives may be much lower).

When executing 518, in whole or in part, functionality associated with the system-directed command (e.g., " . . . please display the chest X-Ray for encounter participant XXX") in response to detecting 516 the occurrence of the specific conversational context (e.g., breathing difficulties; respiratory issues), ambient cooperative intelligence process 10 may recommend 524 the execution of one or more supplemental operations in response to detecting 516 the occurrence of the specific conversational context (e.g., breathing difficulties; respiratory issues).

Specifically, it is foreseeable that the supplemental operations associated 510 with the specific conversational context detected 516 may have issues that need to be addressed. For example, assume that the specific conversational context detected 516 is only associated with a single system-directed command and, therefore, has a very high confidence level. Accordingly and as discussed above, ambient cooperative intelligence process 10 may automatically render the chest X-Ray for encounter participant XXX. However, assume that upon examining metadata associated with the requested chest X-ray (e.g., chest X-ray 136), ambient cooperative intelligence process 10 determines that the requested chest X-ray (e.g., chest X-ray 136) is out-of-date (e.g., 5 years old). Therefore, ambient cooperative intelligence process 10 may recommend 524 the execution of one or more supplemental operations in response to detecting 516 the occurrence of the specific conversational context (e.g., breathing difficulties; respiratory issues). Specifically and as the requested chest X-ray (e.g., chest X-ray 136) is out-of-date, ambient cooperative intelligence process 10 may recommend 524 that an updated chest X-ray be obtained. For example, ambient cooperative intelligence process 10 may ask (e.g., audibly or visually) if encounter participant 226 wishes to order a new chest X-Ray for encounter participant XXX. Alternatively, ambient cooperative intelligence process 10 may automatically order a new chest X-Ray for encounter participant XXX (an action that may need to be subsequently approved by encounter participant 226).

Non-Medical Applications:

As discussed above, while ambient cooperative intelligence process 10 was described above as being utilized to automate the collection and processing of clinical encounter information to generate/store/distribute medical records, this is for illustrative purposes only and is not intended to be a limitation of this disclosure, as other configurations are possible and are considered to be within the scope of this disclosure. Accordingly, such encounter information may include but are not limited to the following examples.

Financial Information:

For example, ambient cooperative intelligence process 10 generally (and/or ACD system 54 specifically) may be configured to automate the collection and processing of financial data that is generated during an encounter in which financial information is discussed. An example of such an encounter may include but is not limited to a meeting between an individual and a financial advisor. For example, ambient cooperative intelligence process 10 may be configured to supplement/complement a financial advisor's knowledge by recommending products, answering questions and making offers based on the conversation that the financial advisor is having with a client in essentially real time, as well as completing various forms, mortgage applications, stock purchase/sale orders, estate planning documents, etc.

Benefits: The benefits achievable by ambient cooperative intelligence process 10 when configured to process financial information may be considerable. For example and as is understandable, financial advisors may not know all things concerning e.g., financial and investment instruments. Accordingly, ambient cooperative intelligence process 10 (when configured to process financial information) may monitor a conversation between the financial advisor and the client. Ambient cooperative intelligence process 10 may then utilize natural language processing and artificial intelligence to identify issues/questions within the conversation and leverage collective knowledge to provide pertinent information to the financial advisor.

For example, assume that a client visits a financial advisor seeking financial advice concerning tax free/tax deferred retirement savings. Accordingly and through the use of the various systems described above (e.g., audio input device 30, display device 32, machine vision input device 34, and audio rendering device 116), ambient cooperative intelligence process 10 (when configured to process financial information) may monitor the conversation between the financial advisor and the client. Assuming that this is the first time that this client is meeting with his financial advisor, the information obtained during this initial meeting may be parsed and used to populate the various fields of a client intake form. For example, the client may identify themself and their name may be entered into the client intake form. Additionally, ambient cooperative intelligence process 10 may be configured to define a voiceprint and/or face print for the client so that e.g. in the future this voiceprint and/or face print may be utilized to authenticate the client's identity when they want to access their data. Additionally, when the client identifies e.g. their age, their marital status, their spouse's name, their spouse's age, and whether or not they have children and (if so) the age of their children, all of this information may be used to populate this client intake form.

Continuing with the above stated example, assume that the client asks about tax-free/tax-deferred retirement savings plans. The financial advisor may then ask them what their income was last year. As ambient cooperative intelligence process 10 may be monitoring this conversation via audio input device 30, ambient cooperative intelligence process 10 may "hear" that the client is interested in tax-free/tax-deferred retirement savings plans and what their income level is. Accordingly and through the use of the above-described natural language processing and artificial intelligence, ambient cooperative intelligence process 10 may determine whether or not the client qualifies for a 401(k) retirement plan, a pre-tax/post-tax traditional IRA plan, and/or a pre-tax/post-tax Roth IRA plan. Upon making such a determination, ambient cooperative intelligence process 10 may provide supplemental information to the financial advisor so that the financial advisor may provide guidance to the client.

For example, ambient cooperative intelligence process 10 may render (on display device 32) a list of the tax-free/tax-deferred retirement savings plans for which the client qualifies. Additionally/alternatively, this information may be audibly rendered (e.g. covertly into an earbud worn by the financial advisor) so that the financial advisor may provide such information to the client.

Accordingly and through the use of such a system, ambient cooperative intelligence process 10 (when configured to process financial information) may monitor the conversation between (in this example) the financial advisor and a client to e.g. gather information and populate client intake forms, generate voice prints and/or face prints for client authentication, listen to inquiries made by the client, and provide responses to those inquiries so that the financial advisor may provide guidance to the client.

Additionally, ambient cooperative intelligence process 10 may be configured to monitor the advice that the financial advisor is providing to the client and confirm the accuracy of the same, wherein covert corrections/notifications may be provided to the financial advisor in the event that the financial advisor misspoke (e.g., advising the client that they qualify for a retirement plan when they actually do not qualify).

Further, ambient cooperative intelligence process 10 may be configured to provide guidance to the financial advisor/client even when such guidance is not sought. For example, if this client said that they have children, ambient cooperative intelligence process 10 may prompt the financial advisor to inquire as to what college savings plans (e.g. 529s) they have in place for their children. And if none are in place, the financial advisor may be prompted to explain the tax benefits of such plans.

Further still, ambient cooperative intelligence process 10 may be configured to covertly provide information to the financial advisor that may assist in building a relationship between the financial advisor and client. For example, assume that the client explained that his wife's name was Jill (during the first meeting between the client and the financial advisor) and the client explained that he and his wife were going to be visiting Italy over the summer. Assume that the client returns to meet with the financial advisor in the fall. During the first visit, ambient cooperative intelligence process 10 may (as discussed above) populate a client intake form that identifies the client spouse as Jill. Further, ambient cooperative intelligence process 10 may make a note that the client and Jill are going to be visiting Italy in the summer of 2020. Assuming that this follow-up meeting is after the summer of 2020, ambient cooperative intelligence process 10 may covertly prompt the financial advisor to ask the client if he and Jill enjoyed Italy, thus enabling the establishment of goodwill between the client and the financial advisor.

Ambient cooperative intelligence process 10 may further be configured to auto-populate forms that may be required based upon the needs of the client. For example, if the client needs to fill out a certain tax form concerning an IRA rollover, ambient cooperative intelligence process 10 may be configured to obtain necessary information based on a conversation between the financial advisor and the client and/or proactively obtain the required information from a datasource accessible by ambient cooperative intelligence process 10, populate the appropriate form needed to effectuate e.g., the IRA rollover with the data obtained from the datasource, and render (e.g. print) the populated form so that the client may execute the same.

Ambient cooperative intelligence process 10 may further be configured to effectuate the functionality of a digital assistant, wherein ambient cooperative intelligence process 10 may monitor the conversation between (in this example) the financial advisor and the client so that items that were mentioned may be flagged for follow-up. For example, assume that during the above-described conversation between the financial advisor and the client that the client stated that they are interested in setting up 529 college savings accounts for their children and they asked the financial advisor to provide them information concerning the same. Accordingly, ambient cooperative intelligence process may enter (e.g. into a client-specific to do list) "Send 529 information to the Smith family". Additionally, in the event that the client says they would like to have a follow-up meeting in three weeks to chat about 529's, ambient cooperative intelligence process 10 may schedule a meeting within the calendar of the financial advisor for such a discussion.

Legal Information:

For example, ambient cooperative intelligence process 10 generally (and/or ACD system 54 specifically) may be configured to automate the collection and processing of legal data that is generated during an encounter in which legal information is discussed. An example of such an encounter may include but is not limited to a meeting between a legal professional and a person whom they are representing. For example, ambient cooperative intelligence process 10 may be configured to supplement/complement a legal professional's knowledge by recommending strategies, answering questions and providing advice based on the conversation that the legal professional is having with their client in essentially real time, as well as completing hearing/deposition transcripts, warrants, court orders/judgements, various applications for the foregoing and other items, etc.

Benefits: The benefits achievable by ambient cooperative intelligence process 10 when configured to process legal information may be considerable. For example and as is understandable, legal professionals may not know all things concerning e.g., various legal situations, events and procedures. Accordingly, ambient cooperative intelligence process 10 (when configured to process legal information) may monitor a conversation between the legal professional and the client. Ambient cooperative intelligence process 10 may then utilize natural language processing and artificial intelligence to identify issues/questions within the conversation and leverage collective knowledge to provide pertinent information to the legal professional.

For example, assume that a deposition is occurring where a defendant in a lawsuit (who is being represented by a first group of attorneys) is being asked questions by the plaintiff in the law suit (who is being represented by a second group of attorneys). Accordingly and through the use of the various systems described above (e.g., audio input device 30, display device 32, machine vision input device 34, and audio rendering device 116), ambient cooperative intelligence process 10 (when configured to process legal information) may monitor the conversation between the defendant/first group of attorneys and the plaintiff/second group of attorneys. In such a situation, ambient cooperative intelligence process 10 (when configured to process legal information) may be configured to effectuate the functionality of a court transcriptionist.

For example, the participants in the deposition may be asked to identify themselves (e.g. provide name and title). Ambient cooperative intelligence process 10 may use this information to populate an attendance log concerning the deposition and may be configured to define a voiceprint and/or face print for each attendee of the deposition.

Accordingly and once the deposition actually starts, ambient cooperative intelligence process 10 may monitor the deposition and may (via the above described voice prints/face prints) diarize the same, essentially replicating the functionality of a court transcriptionist. Basically, ambient cooperative intelligence process 10 may generate a diary of the deposition proceeding that reads like a movie script, wherein e.g. each spoken statement is transcribed and the speaker of that spoken statement is identified (via the voiceprint/face print).

Additionally and through the use of the above-describe natural language processing and artificial intelligence, traditional legal tasks may be efficiently effectuated. For example, suppose that (during the deposition) an objection is made and a piece of case law is cited as the basis for the objection. If the non-objecting attorney believes that this piece of case law is no longer valid (e.g. due to it being overturned by a higher court), the non-objecting attorney may ask ambient cooperative intelligence process 10 (when configured to process legal information) to determine the status of the relied-upon piece of case law (i.e., whether the piece of case law is still valid or has been overturned). Ambient cooperative intelligence process may then provide an answer to the non-objecting attorney (e.g., the case is still valid or the case was overturned by the $1^{st}$ Circuit Court of Appeals in 2016, which was affirmed by the US Supreme Court in 2017).

Telecom Information:

For example, ambient cooperative intelligence process 10 generally (and/or ACD system 54 specifically) may be configured to automate the collection and processing of telecom data that is generated during an encounter between a caller and a sales/service representative. An example of such an encounter may include but is not limited to a telephone call and/or chat session between a sales/service representative and a customer who is having a problem with their cable television service. For example, ambient cooperative intelligence process 10 may be configured to supplement/complement a service representative's knowledge by recommending plans/products, trouble-shooting procedures, answering questions and providing advice based on the conversation that the service representative is having with their customer in essentially real time.

Benefits: The benefits achievable by ambient cooperative intelligence process 10 when configured to process telecom information may be considerable. For example and as is understandable, sales/service representatives may not know all things concerning e.g., various service plans, available products, trouble-shooting procedures, and warranty coverage. Accordingly, ambient cooperative intelligence process 10 (when configured to process telecom information) may monitor a conversation (e.g., voice or text) between the service representative and the caller. Ambient cooperative intelligence process 10 may then utilize natural language processing and artificial intelligence to identify issues/questions within the conversation and leverage collective knowledge to provide pertinent information to the telecom salesperson.

For example, assume that a user of a cable television service is having a difficult time tuning to one of their pay channels within their cable TV channel list. Accordingly, this user may call up (or message) their cable television service and chat with a customer service representative. Ambient cooperative intelligence process 10 (when configured to process telecom information) may e.g. utilize caller ID, IP addresses and/or voice prints to identify the caller and obtain information concerning their account, their location, their equipment, their service plan, etc.

Assume for this example that the caller explains to the service representative that they cannot tune their cable box to the desired channel. Ambient cooperative intelligence process 10 may e.g. first confirm that their current service plan includes the channel that the caller is trying to access. In the event that the service plan does not include such channel, ambient cooperative intelligence process 10 may notify the service representative (e.g. via a text-based message visible on a display accessible by the service representative or via an earbud) that the channel is not included in their service plan. Ambient cooperative intelligence process 10 may then provide information to the service representative concerning which service plans include the channel about which the caller is inquiring to see if e.g., they want to upgrade/change their plan to one that includes the channel in question.

In the event that the channel is indeed included in the current service plan of the caller, ambient cooperative intelligence process 10 may begin to provide prompts to the service representative concerning a troubleshooting procedure that may be utilized to identify the problem. For example, ambient cooperative intelligence process 10 (via e.g. a display or an earbud) may provide the service representative with a sequence of steps that the caller can perform in order to (hopefully) rectify the situation. For example, the service representative may instruct the caller to first unplug the cable box from the electrical outlet and let it sit for 30 seconds and then plug it in so that it may reboot. In the event that this procedure does not fix the problem, the list provided by ambient cooperative intelligence process 10 may instruct the service representative to send a reset signal to the cable box in question. In the event that this procedure does not fix the problem, ambient cooperative intelligence process 10 may determine that a new cable box is needed and may assist the service representative in scheduling a service call so that the faulty cable box may be replaced by a service technician.

Retail Information:

For example, ambient cooperative intelligence process 10 generally (and/or ACD system 54 specifically) may be configured to automate the collection and processing of retail data that is generated during an encounter in which retail information is discussed. An example of such an encounter may include but is not limited to a meeting between a salesclerk at a department store and a person interested in purchasing a particular product. For example, ambient cooperative intelligence process 10 may be configured to supplement/complement a salesclerk's knowledge by recommending products, answering questions and providing advice based upon the conversation that the salesclerk is having with their customer in essentially real time, as well as enabling checkout, completing work order forms, financial/sales agreements, product order forms, warranty forms, etc.

Benefits: The benefits achievable by ambient cooperative intelligence process 10 when configured to process retail information may be considerable. For example and as is understandable, salesclerks may not know all things concerning e.g., the assortment of products offered and the location of the same. Accordingly, ambient cooperative intelligence process 10 (when configured to process retail information) may monitor a conversation between the salesclerk and the customer. Ambient cooperative intelligence process 10 may then utilize natural language processing and artificial intelligence to identify issues/questions within the conversation and leverage collective knowledge to provide pertinent information to the salesclerk.

For example, assume that a customer goes to a local department store and they are looking for several items, including an electric drill. So this customer approaches a salesclerk and asks them if they sell electric drills and, if so, where they are. Ambient cooperative intelligence process 10 (when configured to process retail information) may monitor this conversation and identify the issues that need to be addressed through the use of the above-described natural language processing and artificial intelligence. For example, ambient cooperative intelligence process 10 may identify the phrase "electric drill" within the statement made by the customer and may examine inventory records for the department store and determine that the department store does indeed sell electric drills. Further, ambient cooperative intelligence process 10 may determine that the customer is asking about the location of these electric drills and, upon checking product stocking charts for the department store, may determine that electric drills are in the hardware section (aisle 23, bays 16-20).

Additionally, ambient cooperative intelligence process 10 may be configured to address additional questions that the customer may have, such as 'What electric drills the have that cost under $30?", "What electric drill has the longest warranty?", "What electric drills do you have from DeWalt?" and "Do you have drill bits for drilling into cement?". When providing answers concerning these questions raised by the customer, ambient cooperative intelligence process 10 may overtly provide the information onto a display screen (e.g. a handheld electronic device) so that the customer may review the same. Alternatively, ambient cooperative intelligence process 10 may covertly provide the information in an earbud so that the salesclerk may verbally provide the information to the customer.

Further, assume that a family goes into a local wireless carrier store to inquire about cell phones and cell phone plans. Accordingly and through the use of the various systems described above (e.g., audio input device 30, display device 32, machine vision input device 34, and audio rendering device 116), ambient cooperative intelligence process 10 (when configured to process retail information) may monitor the conversation between the family and salesclerk and provide guidance and insight with respect to such conversation through the use of the above-described natural language processing and artificial intelligence. For example, assume that the family asks the salesclerk if there are any sales/promotions on the latest iPhones. If so, ambient cooperative intelligence process 10 (when configured to process retail information) may covertly provide a list of sales/promotions to the salesclerk via e.g., an earbud assembly or may overly provide a list of sales/promotions to the salesclerk via e.g., a client electronic device (e.g., a smart phone, a tablet, a laptop, or a display).

Additionally, assume that the family inquires as to what is the best phone to buy and/or what is the best data plan to be on when you do extensive international traveling. Accordingly, ambient cooperative intelligence process 10 (when configured to process retail information) may e.g. render a list of applicable phones/data plans on a client electronic device (e.g. a smart phone, a tablet, a laptop, or display) so that such options may be reviewed with the salesclerk. Further, in the event that ambient cooperative intelligence process 10 determines that one or more members of the family is interested in a cellular telephone that is not compatible with the cellular networks in various countries around the world, ambient cooperative intelligence process 10 may prompt the salesclerk to inquire as to whether this family member travels to e.g., Countries A, B or C.

Additionally, as ambient cooperative intelligence process 10 may be monitoring the conversation between the family and the salesclerk, ambient cooperative intelligence process 10 may determine the quantity of cellular telephones they are interested in purchasing. Ambient cooperative intelligence process 10 may then review the various promotional plans being offered by the cell phone manufacturers, as well as any the available data plan options, so that ambient cooperative intelligence process 10 may present the phones and data plans that are most advantageous to the family.

Additionally, ambient cooperative intelligence process 10 may monitor the conversation between the family and the salesclerk to identify and/or correct any mistakes or misrepresentations that the salesclerk may have inadvertently made. For example, if the user said that they often travel to Country X and they are in the process of purchasing Cellular Telephone Y (which is not usable within Country X), ambient cooperative intelligence process 10 may covertly notify (e.g. via an earbud) the salesclerk that Cellular Telephone Y will not function properly within Country X.

General

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:
    monitoring a plurality of conversations to generate a conversation data set;
    processing the conversation data set to:
        define a system-directed command, and
        associate one or more conversational contexts with the system-directed command, wherein associating one or more conversational contexts with the system-directed command includes identifying a subject matter of a conversation preceding an occurrence of a wake-up word/phrase and defining at least one of the conversational contexts based, at least in part, upon the subject matter of the conversation preceding the occurrence of the wake-up word/phrase;
    detecting the occurrence of a specific conversational context, wherein the specific conversational context is included in the one or more conversational contexts associated with the system-directed command, and wherein the system-directed command is determined based, at least in part, upon the at least one of the conversational contexts defined based, at least in part, upon the subject matter of the conversation preceding the occurrence of the wake-up word/phrase; and
    automatically executing, in whole or in part, functionality associated with the system-directed command in response to detecting the occurrence of the specific conversational context without requiring the utterance of the system-directed command and/or the wake-up word/phrase, including processing the conversational context to yield a confidence level with respect to the system-directed command, and automatically executing functionality associated with the system-directed command when the confidence level exceeds a confidence level threshold.

2. The computer-implemented method of claim 1 wherein defining the system-directed command for the ACI system includes:
    monitoring for the occurrence of the wake-up word/phrase;
    identifying a command that follows the wake-up word/phrase; and
    defining the system-directed command as the command that follows the wake-up word/phrase.

3. The computer-implemented method of claim 1 wherein the system-directed command is for an Ambient Cooperative Intelligence (ACI) system.

4. The computer-implemented method of claim 3 wherein the system-directed command is a medical-based command from a medical professional.

5. The computer-implemented method of claim 1 wherein executing, in whole or in part, functionality associated with the system-directed command in response to detecting the occurrence of the specific conversational context includes:
    inquiring about execution of the functionality associated with system-directed command in response to detecting the occurrence of the specific conversational context.

6. The computer-implemented method of claim 1 wherein executing, in whole or in part, functionality associated with the system-directed command in response to detecting the occurrence of the specific conversational context includes:
    recommending the execution of one or more supplemental operations in response to detecting the occurrence of the specific conversational context.

7. A non-transitory computer program product residing on a computer readable medium having a plurality of instructions stored thereon which, when executed by a processor, cause the processor to perform operations comprising:
    monitoring a plurality of conversations to generate a conversation data set;
    processing the conversation data set to:
        define a system-directed command, and
        associate one or more conversational contexts with the system-directed command, wherein associating one or more conversational contexts with the system-directed command includes identifying a subject matter of a conversation preceding an occurrence of a wake-up word/phrase and defining at least one of the conversational contexts based, at least in part, upon the subject matter of the conversation preceding the occurrence of the wake-up word/phrase;
    detecting the occurrence of a specific conversational context, wherein the specific conversational context is included in the one or more conversational contexts associated with the system-directed command, and wherein the system-directed command is determined based, at least in part, upon the at least one of the conversational contexts defined based, at least in part, upon the subject matter of the conversation preceding the occurrence of the wake-up word/phrase; and automatically executing, in whole or in part, functionality associated with the system-directed command in response to detecting the occurrence of the specific conversational context without requiring the utterance of the system-directed command and/or the wake-up word/phrase, including processing the conversational context to yield a confidence level with respect to the system-directed command, and automatically executing functionality associated with the system-directed command when the confidence level exceeds a confidence level threshold.

8. The computer program product of claim 7 wherein defining the system-directed command for the ACI system includes:
monitoring for the occurrence of the wake-up word/phrase;
identifying a command that follows the wake-up word/phrase; and
defining the system-directed command as the command that follows the wake-up word/phrase.

9. The computer program product of claim 8 wherein the system-directed command is for an Ambient Cooperative Intelligence (ACI) system.

10. The computer program product of claim 9 wherein the system-directed command is a medical-based command from a medical professional.

11. The computer program product of claim 8 wherein executing, in whole or in part, functionality associated with the system-directed command in response to detecting the occurrence of the specific conversational context includes:
inquiring about execution of the functionality associated with system-directed command in response to detecting the occurrence of the specific conversational context.

12. The computer program product of claim 8 wherein executing, in whole or in part, functionality associated with the system-directed command in response to detecting the occurrence of the specific conversational context includes:
recommending the execution of one or more supplemental operations in response to detecting the occurrence of the specific conversational context.

13. A computing system including a processor and memory configured to perform operations comprising:
monitoring a plurality of conversations to generate a conversation data set;
processing the conversation data set to:
define a system-directed command, and
associate one or more conversational contexts with the system-directed command, wherein associating one or more conversational contexts with the system-directed command includes identifying a subject matter of a conversation preceding an occurrence of a wake-up word/phrase and defining at least one of the conversational contexts based, at least in part, upon the subject matter of the conversation preceding the occurrence of the wake-up word/phrase;
detecting the occurrence of a specific conversational context, wherein the specific conversational context is included in the one or more conversational contexts associated with the system-directed command, and wherein the system-directed command is determined based, at least in part, upon the at least one of the conversational contexts defined based, at least in part, upon the subject matter of the conversation preceding the occurrence of the wake-up word/phrase; and
automatically executing, in whole or in part, functionality associated with the system-directed command in response to detecting the occurrence of the specific conversational context without requiring the utterance of the system-directed command and/or the wake-up word/phrase, including processing the conversational context to yield a confidence level with respect to the system-directed command, and automatically executing functionality associated with the system-directed command when the confidence level exceeds a confidence level threshold.

14. The computing system of claim 13 wherein defining the system-directed command for the ACI system includes:
monitoring for the occurrence of the wake-up word/phrase;
identifying a command that follows the wake-up word/phrase; and
defining the system-directed command as the command that follows the wake-up word/phrase.

15. The computing system of claim 13 wherein the system-directed command is for an Ambient Cooperative Intelligence (ACI) system.

16. The computing system of claim 15 wherein the system-directed command is a medical-based command from a medical professional.

17. The computing system of claim 13 wherein executing, in whole or in part, functionality associated with the system-directed command in response to detecting the occurrence of the specific conversational context includes:
inquiring about execution of the functionality associated with system-directed command in response to detecting the occurrence of the specific conversational context.

18. The computing system of claim 13 wherein executing, in whole or in part, functionality associated with the system-directed command in response to detecting the occurrence of the specific conversational context includes:
recommending the execution of one or more supplemental operations in response to detecting the occurrence of the specific conversational context.

* * * * *